United States Patent
Holroyd et al.

(10) Patent No.: US 12,329,934 B2
(45) Date of Patent: *Jun. 17, 2025

(54) DEVICES FOR INJECTING MEDICAMENTS AND METHODS OF USE

(71) Applicant: McDermott Laboratories Limited, Dublin (IE)

(72) Inventors: Michael John Holroyd, Cambridge (GB); Robin Craig Cocker, Nottingham (GB); James Terrence Collins, Peterborough (GB); Paul Christopher Edward Mutti, Spilsby (GB); Daniel Colin Jackson, Royston (GB); Michael Edgar Newton, Diss (GB)

(73) Assignee: McDermott Laboratories Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/590,332

(22) Filed: Feb. 28, 2024

(65) Prior Publication Data
US 2024/0197992 A1 Jun. 20, 2024

Related U.S. Application Data

(63) Continuation of application No. 16/980,253, filed as application No. PCT/IB2019/000243 on Mar. 12, 2019, now Pat. No. 12,023,468.
(Continued)

(51) Int. Cl.
*A61M 5/20* (2006.01)
*A61M 5/315* (2006.01)
(Continued)

(52) U.S. Cl.
CPC ............ *A61M 5/20* (2013.01); *A61M 5/2033* (2013.01); *A61M 5/31591* (2013.01);
(Continued)

(58) Field of Classification Search
CPC .. A61M 5/20; A61M 5/31591; A61M 5/3204; A61M 5/326; A61M 5/3271;
(Continued)

(56) References Cited

U.S. PATENT DOCUMENTS

| 8,496,619 B2 | 7/2013 | Kramer et al. |
| 8,708,968 B2 | 4/2014 | Julian et al. |

(Continued)

FOREIGN PATENT DOCUMENTS

| EP | 2361648 | 8/2011 |
| EP | 2361648 A1 | 8/2011 |

(Continued)

OTHER PUBLICATIONS

Notice of Allowance issued Feb. 18, 2022 by the Eurasian Patent Office in corresponding Eurasian patent application No. 202092129. English translation provided.
(Continued)

*Primary Examiner* — James D Ponton
*Assistant Examiner* — Hong-Van N Trinh
(74) *Attorney, Agent, or Firm* — Sorell, Lenna & Schmidt, LLP

(57) ABSTRACT

A device for injecting a medicament is provided. The device has a housing with a container within it which can hold a medicament. At its proximal end the container has a needle and a stopper. The device includes a plunger which at one end can engage the stopper. At the opposite end, the plunger can engage a first resilient member to move the stopper within the container to inject the medicament from the container. The device includes a collar with distal and (Continued)

proximal ends, the distal end engaging with a carriage and causing its rotation and the proximal end engaging with a second resilient member. The second resilient member can engage with a skin sensor which has distal and proximal ends. At the proximal end, the skin sensor can contact an injection site. The housing has a cap which can reduce or prevent movement of the skin sensor.

21 Claims, 36 Drawing Sheets

Related U.S. Application Data

(60) Provisional application No. 62/642,281, filed on Mar. 13, 2018.

(51) Int. Cl.
*A61M 5/32* (2006.01)
*A61M 5/24* (2006.01)

(52) U.S. Cl.
CPC ........ *A61M 5/3202* (2013.01); *A61M 5/3204* (2013.01); *A61M 5/326* (2013.01); *A61M 2005/2013* (2013.01); *A61M 2005/2403* (2013.01); *A61M 2005/2488* (2013.01); *A61M 2005/3267* (2013.01)

(58) Field of Classification Search
CPC ............ A61M 5/2422; A61M 5/31501; A61M 5/3243; A61M 5/2033; A61M 5/3202; A61M 2005/2013; A61M 2005/2403; A61M 2005/2488; A61M 2005/208; A61M 2005/3267
See application file for complete search history.

(56) References Cited

U.S. PATENT DOCUMENTS

| | | |
|---|---|---|
| 8,814,834 B2 | 8/2014 | Sund et al. |
| 8,939,943 B2 | 1/2015 | Edwards et al. |
| 8,992,477 B2 | 3/2015 | Raday et al. |
| 9,022,022 B2 | 5/2015 | Edwards et al. |
| 9,339,610 B2 | 5/2016 | Julian et al. |
| 9,352,090 B2 | 5/2016 | Brereton et al. |
| 9,364,610 B2 | 6/2016 | Kramer et al. |
| 9,364,611 B2 | 6/2016 | Kramer et al. |
| 9,408,976 B2 | 8/2016 | Olson et al. |
| 9,446,195 B2 | 9/2016 | Kramer et al. |
| 9,604,003 B2 | 3/2017 | Brereton et al. |
| 9,623,181 B2 | 4/2017 | Brereton et al. |
| 9,867,949 B2 | 1/2018 | Sund et al. |
| 9,950,123 B2 | 4/2018 | Brereton et al. |
| 10,022,503 B2 | 7/2018 | Julian et al. |
| 10,143,792 B2 | 12/2018 | Edwards et al. |
| 10,149,939 B2 | 12/2018 | Giambattista et al. |
| 10,279,131 B2 | 5/2019 | Kramer et al. |
| 10,322,239 B2 | 6/2019 | Edwards et al. |
| 10,357,609 B2 | 7/2019 | Kramer et al. |
| 10,420,898 B2 | 9/2019 | Daniel |
| 10,449,303 B2 | 10/2019 | Olson et al. |
| 10,456,531 B2 | 10/2019 | Olson et al. |
| 10,688,244 B2 | 6/2020 | Edwards et al. |
| 10,806,867 B2 | 10/2020 | Raday et al. |
| 10,894,127 B2 | 1/2021 | Tschirren et al. |
| 10,894,132 B2 | 1/2021 | Brereton et al. |
| 10,905,827 B2 | 2/2021 | Kramer et al. |
| 10,933,197 B2 | 3/2021 | Daniel |
| 11,033,684 B2 | 6/2021 | Knudsen et al. |
| 11,077,257 B2 | 8/2021 | Kemp |
| 11,185,642 B2 | 11/2021 | Kramer et al. |
| 11,793,938 B2 | 10/2023 | Holroyd et al. |
| 2013/0296794 A1 | 11/2013 | Brereton ............. A61M 5/2033 604/197 |
| 2013/0324925 A1 | 12/2013 | Brereton ................. A61M 5/46 604/110 |
| 2014/0207106 A1 | 7/2014 | Bechmann et al. |
| 2015/0224259 A1 | 8/2015 | Giambattista ....... A61M 5/2448 604/207 |
| 2017/0136189 A1 | 5/2017 | Tschirren ............ A61M 5/3204 |
| 2017/0203048 A1 | 7/2017 | Chevalier |
| 2017/0209647 A1 | 7/2017 | Daniel |
| 2017/0323382 A1 | 11/2017 | Ohlsson |
| 2017/0348487 A1 | 12/2017 | Bechmann .......... A61M 5/3204 |
| 2018/0304014 A1 | 10/2018 | Knudsen et al. |
| 2018/0353711 A1 | 12/2018 | Kim et al. |
| 2019/0151565 A1 | 5/2019 | Groetzbach et al. |
| 2019/0290848 A1 | 9/2019 | Kramer et al. |
| 2019/0374717 A1 | 12/2019 | Swanson et al. |
| 2020/0016329 A1 | 1/2020 | Schabbach et al. |
| 2020/0069886 A1 | 3/2020 | Zhang et al. |
| 2020/0101229 A1 | 4/2020 | Plambech et al. |
| 2020/0155763 A1 | 5/2020 | Wilmot et al. |
| 2020/0282144 A1 | 9/2020 | Pearson |
| 2020/0297930 A1 | 9/2020 | Hommann et al. |
| 2020/0316298 A1 | 10/2020 | Hourmand et al. |
| 2020/0324051 A1 | 10/2020 | Atterbury et al. |
| 2020/0360612 A1 | 11/2020 | Gazeley et al. |
| 2020/0376200 A1 | 12/2020 | Zucker et al. |
| 2020/0398002 A1 | 12/2020 | Mesa et al. |
| 2020/0405973 A1 | 12/2020 | Raday et al. |
| 2021/0085881 A1 | 3/2021 | Daniel |
| 2021/0085882 A1 | 3/2021 | Daniel |
| 2021/0085883 A1 | 3/2021 | Daniel |
| 2021/0196890 A1 | 7/2021 | Appy et al. |
| 2021/0252222 A1 | 8/2021 | Kramer et al. |
| 2022/0080131 A1 | 3/2022 | Kramer et al. |

FOREIGN PATENT DOCUMENTS

| | | |
|---|---|---|
| EP | 3116568 | 7/2021 |
| EP | 2654840 | 4/2022 |
| JP | 2014526297 A | 10/2014 |
| WO | 2013012745 | 1/2013 |
| WO | 2015138261 | 9/2015 |
| WO | WO 2019/237082 | 12/2019 |
| WO | WO 2019/239384 | 12/2019 |
| WO | WO 2020/173994 | 9/2020 |

OTHER PUBLICATIONS

Written Opinion issued Apr. 15, 2022 by the IP Office of Singapore in corresponding Singapore patent application No. 11202008834S.
International Search Report of the International Searching Authority (ISA/EPO) dated Jul. 10, 2019 issued in PCT/IB2019/000243 filed Mar. 12, 2019.
Written Opinion of the International Searching Authority (ISA/EPO) dated Jul. 10, 2019 issued in PCT/IB2019/000243 filed Mar. 12, 2019.

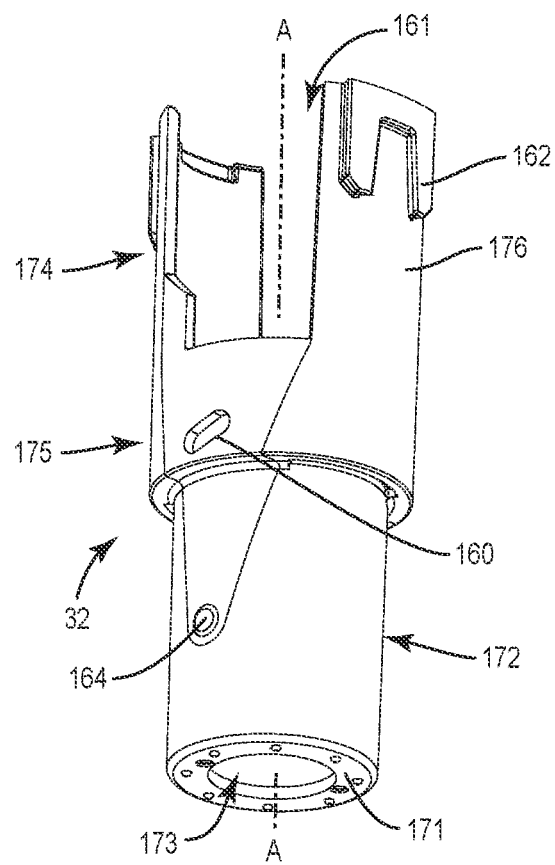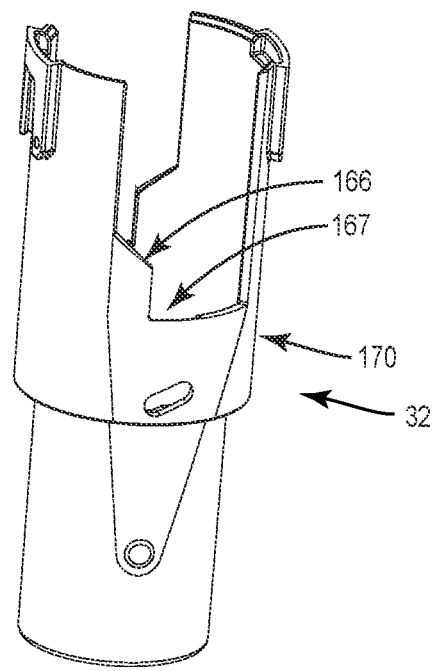
FIG. 7A
FIG. 7B
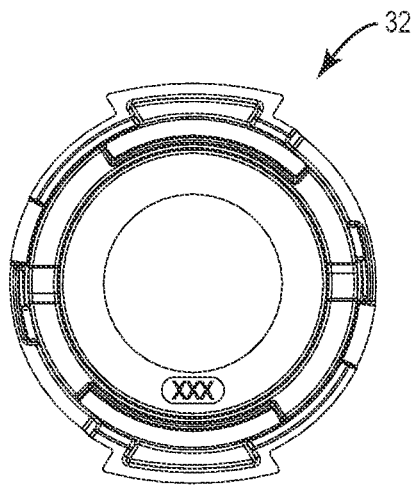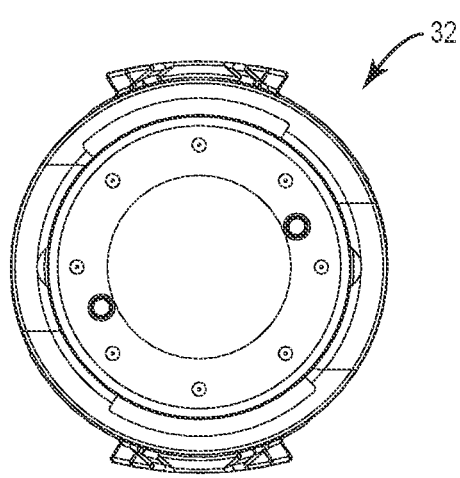
FIG. 7C  FIG. 7D

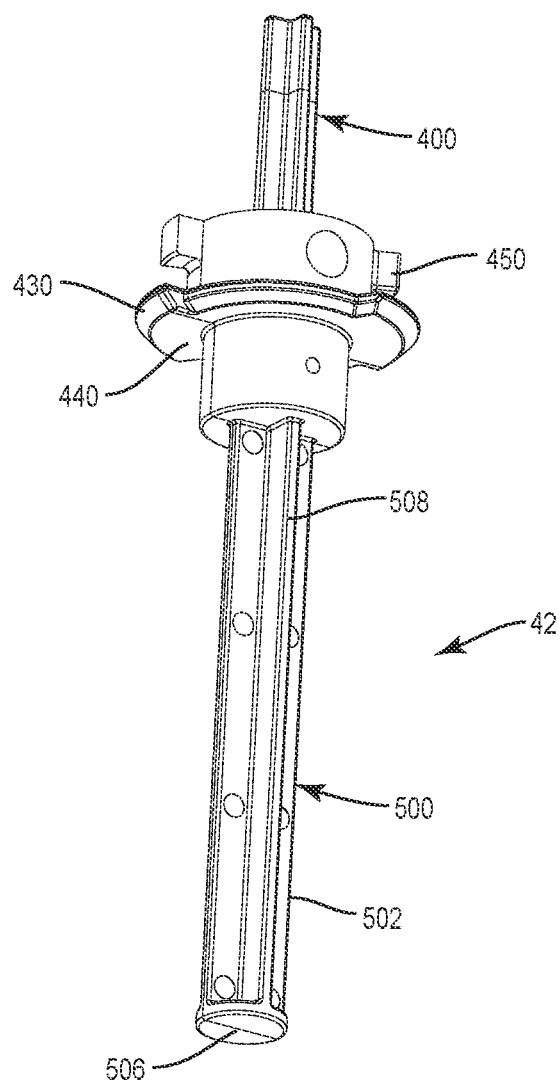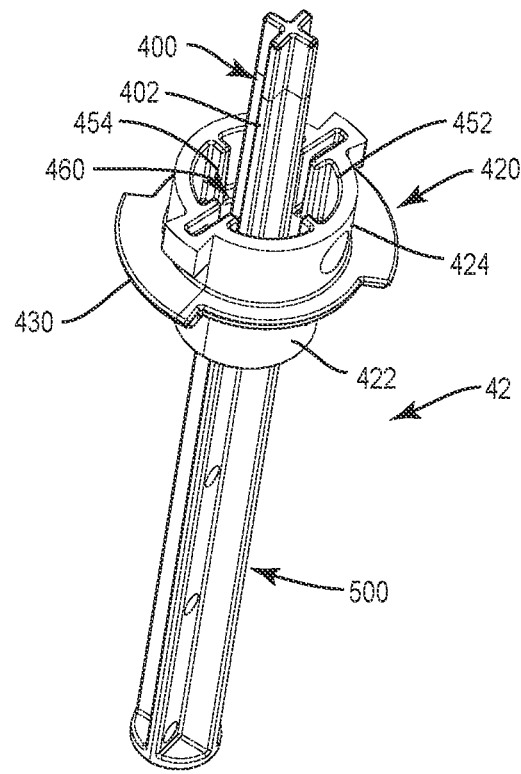
*FIG. 13A*          *FIG. 13B*
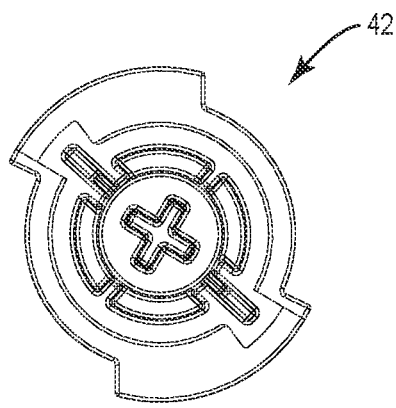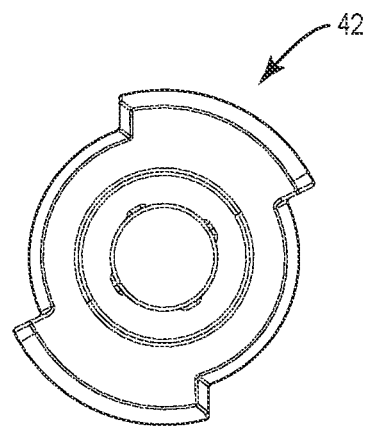
*FIG. 13C*          *FIG. 13D*

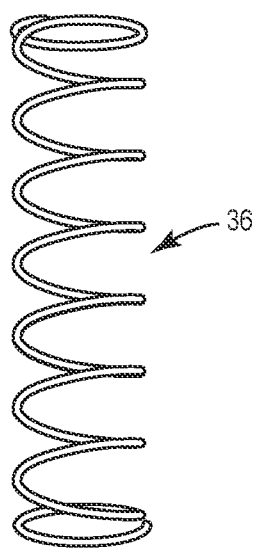
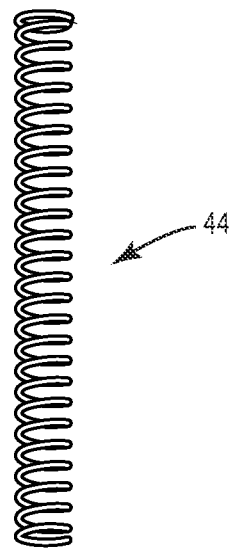
FIG. 16A  FIG. 16B
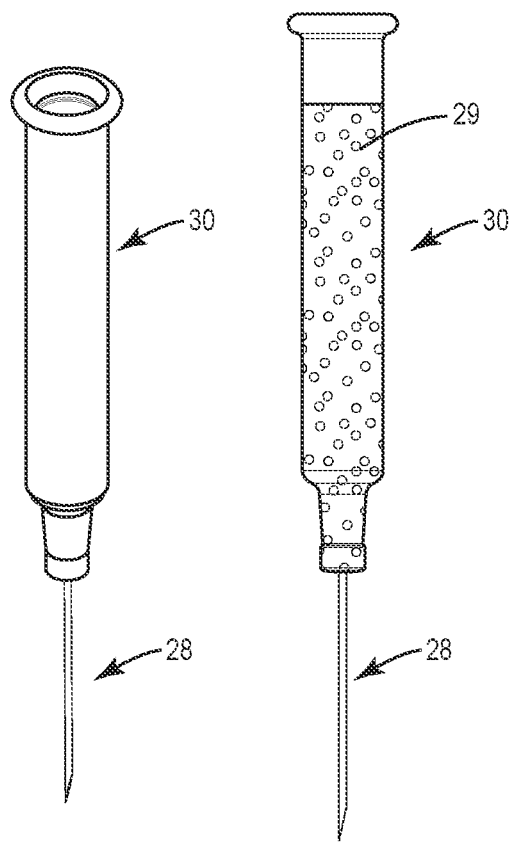
FIG. 17A  FIG. 17B
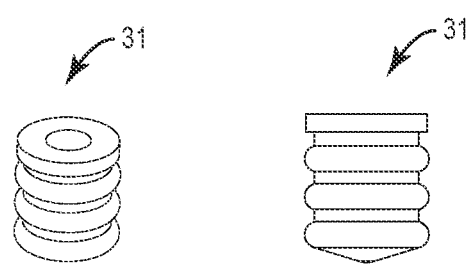
FIG. 17C  FIG. 17D

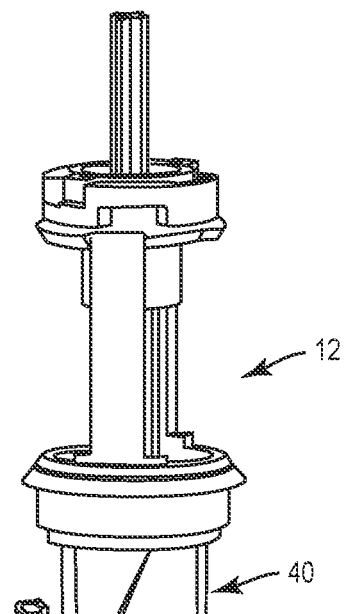
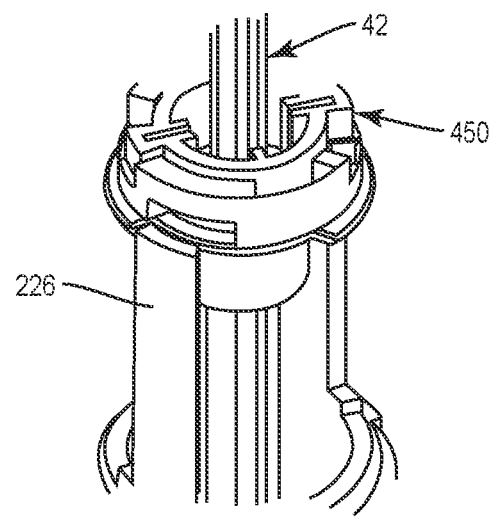
*FIG. 23C*
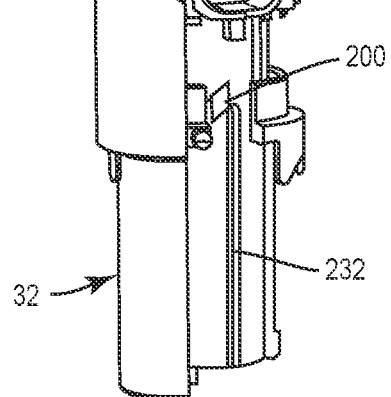
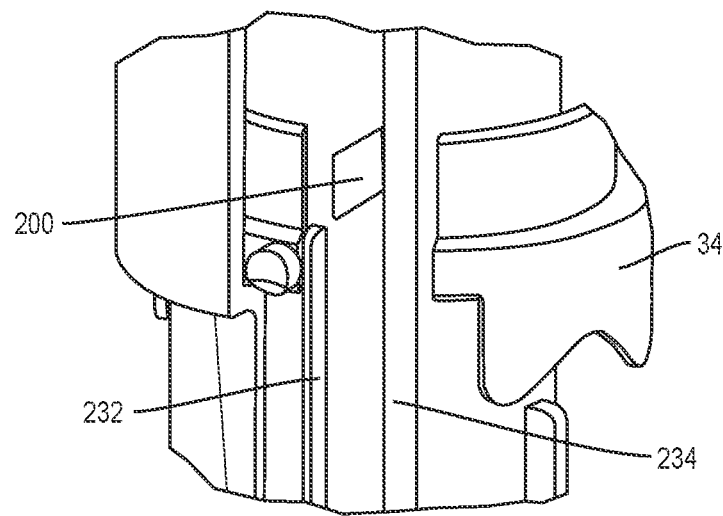
*FIG. 23A*     *FIG. 23B*

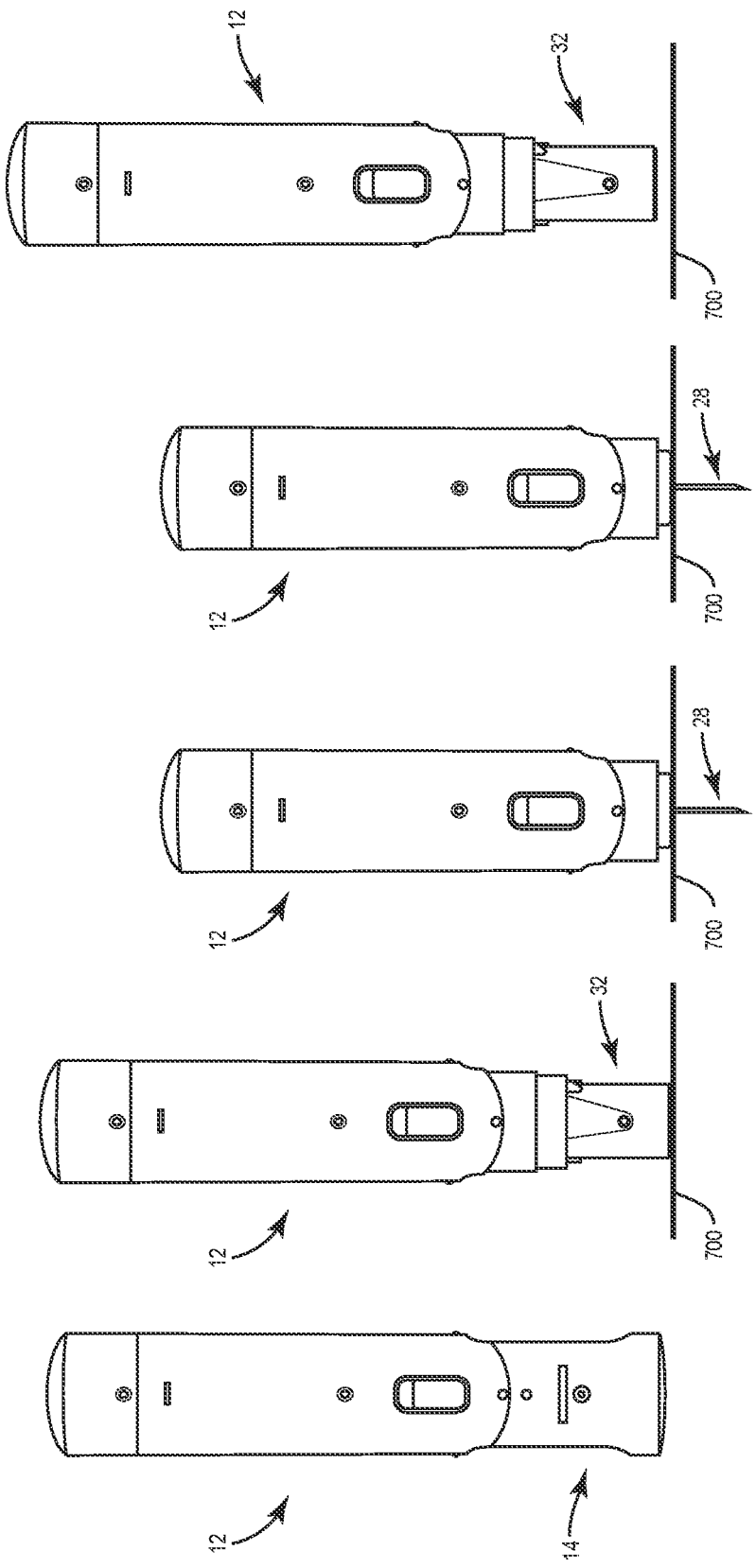

DEVICES FOR INJECTING MEDICAMENTS AND METHODS OF USE

This application claims the benefit of the filing of U.S. Provisional Patent Application Ser. No. 62/642,281, entitled "DELIVERY DEVICE AND METHOD" filed on Mar. 13, 2018, the contents of which are hereby incorporated by reference in their entirety.

BACKGROUND

Autoinjectors are medicament delivery devices that facilitate injection of a predetermined dosage of medication. Autoinjectors are particularly beneficial for self-administration by patients, or administration by untrained personnel.

Typically, autoinjectors allow the user more control over the injection process as the user can pick the injection site and inject the medication. Having more control over the injection process may reduce the hesitation, pain and anxiety associated with needles and may also enhance patient compliance with the particular medication.

Often times, autoinjectors can be useful in treating acute or chronic conditions. For example, in a chronic condition such as diabetes, autoinjectors can hold a specific dose of insulin. With the added control from an autoinjector, and the specific dose of insulin, patient compliance can be enhanced, and an inaccurate dose of medication administered to the patient can be avoided.

In acute conditions, such as in the acute treatment of migraines, some patients are instructed to administer an emergency injection of a selective serotonin receptor agonist, such as for example, sumatriptan to be injected at the onset of the migraine. The autoinjector allows the patient control for the self and accurate administration of the medication to alleviate the migraine, even when the patient is faced with the pain and visual disturbances that are often associated with a debilitating migraine.

Typically, autoinjector devices have one or more specific doses of the medication pre-loaded in a container, such as a syringe. The syringe is coupled to a needle for the patient to puncture the skin and a plunger to expel the medication from the syringe and out of the needle to the injection site.

After the injection occurs and the medication has been expelled from the syringe, some autoinjectors have a needle guard or a skin sensor that can be deployed and cover the needle after injection to help reduce or prevent further puncture injury from the needle or re-use of the needle.

Sometimes, autoinjectors having a needle guard or skin sensor can be unreliable and the needle guard or skin sensor can deploy improperly or jam and prevent medicament administration. This can be a severe problem especially in a life-threatening situation, when the medicament is needed urgently.

It is therefore desirable to provide new devices for injecting medicaments and methods that provide a reliable and safe injection to the user. Devices for injecting a medicament and methods that allow accurate delivery of the medicament to the injection site, which can be used even by untrained personnel would be most beneficial.

SUMMARY

New devices for injecting a medicament and methods are described that provide a reliable and safe injection to the user. The devices for injecting a medicament and methods provided allow accurate delivery of the medicament to the injection site and can be used even by untrained personnel.

The delivery devices and methods described include a housing which has a proximal end and a distal end. The housing has a container disposed within it which is configured to hold a medicament. In some aspects, the container can be a syringe and has a needle at a proximal end and a stopper disposed within the container. At the distal end, the container is coupled to a plunger which can have a distal end and a proximal end. In some embodiments, at the proximal end, the plunger is configured to engage the stopper, the distal end of the plunger is configured to engage an energy storage member and move the stopper within the container to inject the medicament from the container and out of the needle. The energy storage member can be a first and/or a second resilient member. In some aspects, the first resilient member can be a spring. The device also has a carriage which has at least a portion of the container disposed therein, the carriage rotatable relative to the housing. The device further includes a collar having a distal end and a proximal end, the distal end of the collar configured to engage the carriage and cause rotation of the carriage, the proximal end of the collar configured to engage a second resilient member, which in some aspects can be a spring. The device includes a skin sensor which has a distal end and a proximal end, the distal end of the skin sensor configured to engage the second resilient member, and the proximal end of the skin sensor configured to contact an injection site. A cap configured to engage the proximal end of the housing can reduce or prevent the movement of the skin sensor when the device is in an initial storage state.

In some embodiments, when the cap is removed from the housing of the device, and an injection force is applied to the skin sensor, the second resilient member is compressed and engages the collar causing the collar to rotate the carriage. On rotation of the carriage, the first resilient member engages the plunger to inject the medicament from the container and out of the needle.

In various aspects, the device of this disclosure is disposable and comprises a single dose of medicament. In some aspects, the skin sensor is configured to retract when the needle is injected and extend to surround the needle after the medicament is injected to protect the user from accidental needlestick injuries. In other aspects, the first resilient member, which can be a spring, is in a compressed state before an injection force is applied to the skin sensor. In yet other embodiments, the distal end of the plunger comprises a restraining member, the restraining member configured to reduce or prevent movement of the plunger and is configured to hold the first resilient member in a compressed state.

The rotation of the carriage causes the rotation of the restraining member of the plunger which causes the first resilient member to decompress and allow the plunger to move the stopper within the container or syringe to inject the medicament from the container and out of the needle.

In various embodiments, the needle of the container is protected by a needle shield at the proximal end. The needle shield can be made of a flexible material relative to the housing and/or can be a rigid material relative to the first or second resilient member.

The device, in many aspects, can further include a cap insert coupled to the cap. The cap insert can have a capture member for the needle shield, the capture member being configured for removing the needle shield of the needle when the cap is removed from the housing.

In some aspects, the device further comprises a skin sensor insert coupled to the skin sensor, the skin sensor insert configured to couple with the cap insert. In other aspects, the skin sensor insert is not configured to couple with the cap insert. In other aspects, the skin sensor insert comprises a locking surface configured to lock with a locking surface of the cap before the cap is removed. In various embodiments, the lock-driving surface of the skin sensor insert is a W shaped cam and the locking surface of the cap is a triangular shaped cam which couples to the W shaped cam of the skin sensor insert. In other aspects, the locking surfaces are the U-shaped slot 237 and skin sensor insert surfaces as described below.

This disclosure also provides a method of injecting a dose of a medicament, the method comprising injecting a dose of the medicament at an injection site using an injection device, the injection device comprising a housing having a proximal end, the housing having a container disposed within the housing, the container configured to hold a medicament, the container having a needle at a proximal end, and a stopper disposed within the container; a plunger having a distal end and a proximal end, the proximal end of the plunger configured to engage the stopper, the distal end of the plunger configured to engage a first resilient member and move the stopper within the container to inject the medicament from the container and out of the needle; a carriage having at least a portion of the container disposed therein, the carriage rotatable relative to the housing; a collar having a distal end and a proximal end, the distal end of the collar configured to engage the carriage and cause rotation of the carriage, the proximal end of the collar configured to engage a second resilient member; a skin sensor having a distal end and a proximal end, the distal end of the skin sensor configured to engage the second resilient member, and the proximal end of the skin sensor configured to contact a skin site; and a cap configured to engage the proximal end of the housing to prevent movement of the skin sensor. In various embodiments, the cap from the housing is removed prior to injecting the dose of the medicament at an injection site. The removal of the cap uncovers the skin sensor which can be applied to the injection site with an injection force to cause the needle to pierce the skin of a patient allowing the medicament to be injected from the container through the needle. Subsequently, the needle is withdrawn from the injection site. In various embodiments, the application of the skin sensor to the injection site and the withdrawal of the needle from the injection site are performed manually.

This disclosure also provides for a removable cap for a device for injecting a medicament. In some embodiments, the cap can be that of an autoinjector and can comprise a tubular body having a substantially oval cross-sectional profile, the tubular body having a proximal end and a distal end, the proximal end configured to receive a cap insert for covering the tubular body of the cap and the distal end configured to receive a housing of the device. In various aspects, the cap further comprises grip features at the distal end of the tubular body and lock lugs or cams for providing a locking mechanism for the device. In other aspects, the cap comprises a recess for retention of the housing of the device. The cap insert of the device, in several aspects, comprises a cover, a cap insert body and a capture member for a needle shield of a needle attached to a container, the container disposed within the housing of the device. In many aspects, the capture member is a tubular shaft centrally disposed along a longitudinal axis on the cover of the cap, the tubular shaft further comprising clip hooks configured for engaging the needle shield of the needle. The cap insert also comprises two arms having opposed inner concave surfaces and disposed around the capture member of the cap insert configured to engage with the proximal end of the cap.

In various embodiments, the cap is configured to engage the proximal end of the housing and the skin sensor, the cap having a locking surface configured to lock with a locking surface of the skin sensor to prevent the movement of the skin sensor. In some aspects, the locking surface of the cap comprises a recess or projection, and the skin sensor further comprises a skin sensor insert, the skin sensor insert comprising a recess or projection that locks with the recess or projection of the locking surface of the cap. In other aspects, the recess or projection of the cap is a triangular shaped cam and the recess or projection of the skin sensor insert is a W shaped cam configured to couple with the triangular shaped cam of the cap. In many aspects, the skin sensor insert comprises lugs configured to engage a U-slot in the carriage and/or slots in the skin sensor.

In various aspects, the carriage of the device described in this disclosure includes a tubular body having a proximal end and a distal end, a lower portion at the proximal end and an upper portion at the distal end, the upper portion having a base, the base having a lower rim, an upper rim and two arms extending from the upper rim, the arms facing each other to form a U-shape with the upper rim and the carriage configured to receive a medicament container. In many aspects, the carriage can be monolithic. In many aspects, at its proximal end, the carriage includes an abort rail, an injection rail and a lock or inverted J rail, all rails spaced apart and next to one another, wherein the abort rail is disposed between the lock rail and the injection rail. In various embodiments, the lock rail includes a U-shaped slot configured to engage the lugs of the skin sensor insert to prevent the skin sensor from moving when the device is dropped or shocked. In many aspects, when the cap is removed from the housing, the second resilient member drives the needle guard insert down a slope of the U-shaped slot and out of engagement with the lock rail.

In many embodiments, the skin sensor insert further includes an external pin and the skin sensor comprises an external slot and a cam face configured to allow the external pin of the skin sensor insert to run along the cam face of the skin sensor and engage with the slot of the skin sensor on assembly. In some aspects, at its distal end the skin sensor further comprises a cam for engagement with the collar. In other aspects, at its distal end the collar further comprises a threshold face, the cam of the skin sensor causes the threshold face of the collar to rotate and engage with the carriage to generate a threshold force, which can vary from about 9 N to about 23 N.

This disclosure also provides a method of injecting a dose of a medicament, the method comprising injecting a dose of the medicament at an injection site using an injection device, the injection device comprising a housing having a proximal end, the housing having a container disposed within the housing, the container configured to hold a medicament, the container having a needle at a proximal end, and a stopper disposed within the container; a plunger having a distal end and a proximal end, the proximal end of the plunger configured to engage the stopper, the distal end of the plunger configured to engage a first resilient member and move the stopper within the container to dispense the medicament from the container and out of the needle; a carriage having at least a portion of the container disposed therein, the carriage rotatable relative to the housing; a collar having a distal end and a proximal end, the distal end of the collar configured to engage the carriage and cause rotation of the carriage, the proximal end of the collar configured to engage a second resilient member; a skin sensor having a distal end and a proximal end, the distal end of the skin sensor configured to engage the second resilient member, and the proximal end of the skin sensor configured to contact skin; and a cap configured to engage the proximal end of the housing and the skin sensor, the cap having a locking surface configured to lock with a locking surface of the skin sensor to prevent movement of the skin sensor.

In various embodiments, the carriage of the device described in this disclosure has at least a portion that engages a constrainer, the constrainer at least partially disposed within the carriage and holding the container therein, the constrainer having audible and/or tactile feedback member to indicate the medicament dispensing, the carriage being rotatable relative to the housing. In many aspects, the constrainer comprises a cylindrical body and a wing member. The cylindrical body of the constrainer has a proximal end and a distal end and is configured to contact the container at the proximal end and to contact the plunger at the distal end. The wing member of the constrainer body extends along a longitudinal axis of the cylindrical body of the constrainer and comprises a feedback arm, a wing body, and a bridge member connecting the body to the wing member. In various embodiments, the constrainer is monolithic.

In many embodiments, the constrainer further comprises a retaining clip between the proximal end and distal end of its cylindrical body, which retaining clip is configured to suspend the container or, in some aspects, a syringe in the carriage. In some embodiments, the cylindrical body of the constrainer has a cutout around the retaining clip of the container, wherein the cutout is substantially rectangular forming a U shape around the retaining clip of the constrainer. In other aspects, the retaining clip is a rectangular piece on the periphery of the circumference of the body of the constrainer. In many aspects, the retaining clip comprises a body having a distal end adjacent to the distal end of the constrainer body and a proximal end adjacent to a cutout in the constrainer body. The body of the retaining clip has a tapered and/or arcuate surface pointing toward an inner surface of the constrainer body. In other aspects, the retaining clip further comprises a tab portion extending toward the inner surface of the constrainer body.

In various embodiments, the wing body of the wing member of the constrainer is substantially rectangular. The wing body comprises a first surface, a second surface opposite the first surface and a side surface disposed between the first and second surfaces, the first surface has a feedback arm and a bridge member connected to the wing body and the second surface may have grooves and ridges. In many aspects, the first and the second surfaces are substantially rectangular. In other embodiments, the bridge member of the first surface bisects the wing body defining an upper wing above the cylindrical body and a lower wing below the cylindrical body of the constrainer.

In many embodiments, the feedback arm of the wing member of the constrainer comprises an upper arm, a lower arm and an elbow joint connecting the upper arm and the lower arm. In other embodiments, the upper arm comprises a first end adjacent to the first surface of the upper wing and a second end comprising a tip which protrudes past the elbow joint to form an L-shape with the lower arm such that the lower arm is longer than the tip of the upper arm. In many aspects, the feedback arm extends toward the constrainer body such that a U-shape is formed between the upper arm, the lower arm and the constrainer body. In some aspects, the bridge member comprises a rectangular arm and a triangular support, wherein the triangular support abuts the first surface of the lower wing. In various embodiments, the constrainer is configured to produce the audible and/or tactile sound providing a signal that the plunger has been activated to push the medicament inside the container and out of the needle when the plunger contacts the U-shape opening of the feedback arm. In many aspects, the feedback arm is flexible relative to the housing such that an upper portion of the plunger is configured to move past the feedback arms. In other aspects, the upper arm of the feedback arm is configured to expand horizontally away from the constrainer body allowing the plunger to move longitudinally in the container.

The disclosure also provides a method of injecting a dose of medicament, the method comprising injecting a dose of medicament at an injection site using an injection device, the injection device comprising a housing having a proximal end, the housing having a container disposed within the housing, the container configured to hold a medicament, the container having a needle at a proximal end, and a stopper disposed within the container; a plunger having a distal end and a proximal end, the proximal end of the plunger configured to engage the stopper, the distal end of the plunger configured to engage a first resilient member and move the stopper within the container to dispense the medicament from the container and out of the needle; a carriage having at least a portion that engages a constrainer, the constrainer at least partially disposed within the carriage and holding the container therein, the constrainer having audible and/or tactile feedback member to indicate the medicament dispensing, the carriage rotatable relative to the housing; a collar having a distal end and a proximal end, the distal end of the collar configured to engage the carriage and cause rotation of the carriage, the proximal end of the collar configured to engage a second resilient member; a skin sensor having a distal end and a proximal end, the distal end of the skin sensor configured to engage the second resilient member, and the proximal end of the skin sensor configured to contact skin; and a cap configured to engage the proximal end of the housing to prevent movement of the skin sensor.

Other features and advantages of the present disclosure will become apparent from the following detailed description. It should be understood, however, that the detailed description and the specific examples, while indicating several embodiments of the disclosure, are given by way of illustration only, since various changes and modifications within the spirit and scope of the disclosure will become apparent to those skilled in the art from this detailed description.

BRIEF DESCRIPTION OF THE FIGURES

In part, other aspects, features, benefits and advantages of the embodiments will be apparent with regard to the following description, appended claims, and accompanying drawings.

FIGS. 7A and 7B are perspective views of a skin sensor of the autoinjector in FIG. 2;

FIGS. 7C and 7D are top and bottom views, respectively, of the skin sensor illustrated in FIGS. 7A and 7B;

FIGS. 13A and 13B are perspective views of a plunger of the device in FIG. 2;

FIGS. 13C and 13D are top and bottom views, respectively, of the plunger illustrated in FIGS. 13A and 13B;

FIGS. 16A and 16B are perspective views of a skin sensor spring and a plunger spring, respectively, of the device in FIG. 2;

FIGS. 17A and 17B are a perspective view and side view, respectively, of a syringe or container of the device in FIG. 3;

FIGS. 17C and 17D are a perspective view and side view, respectively, of a stopper of the device in FIG. 3;

FIGS. 23A, 23B and 23C are perspective views of components of an embodiment of the device in FIG. 3;

FIGS. 37A, 37B, 37C, 37D and 37E are illustrations of the injection phase cycle of the autoinjector of FIG. 1.

Figure 1:
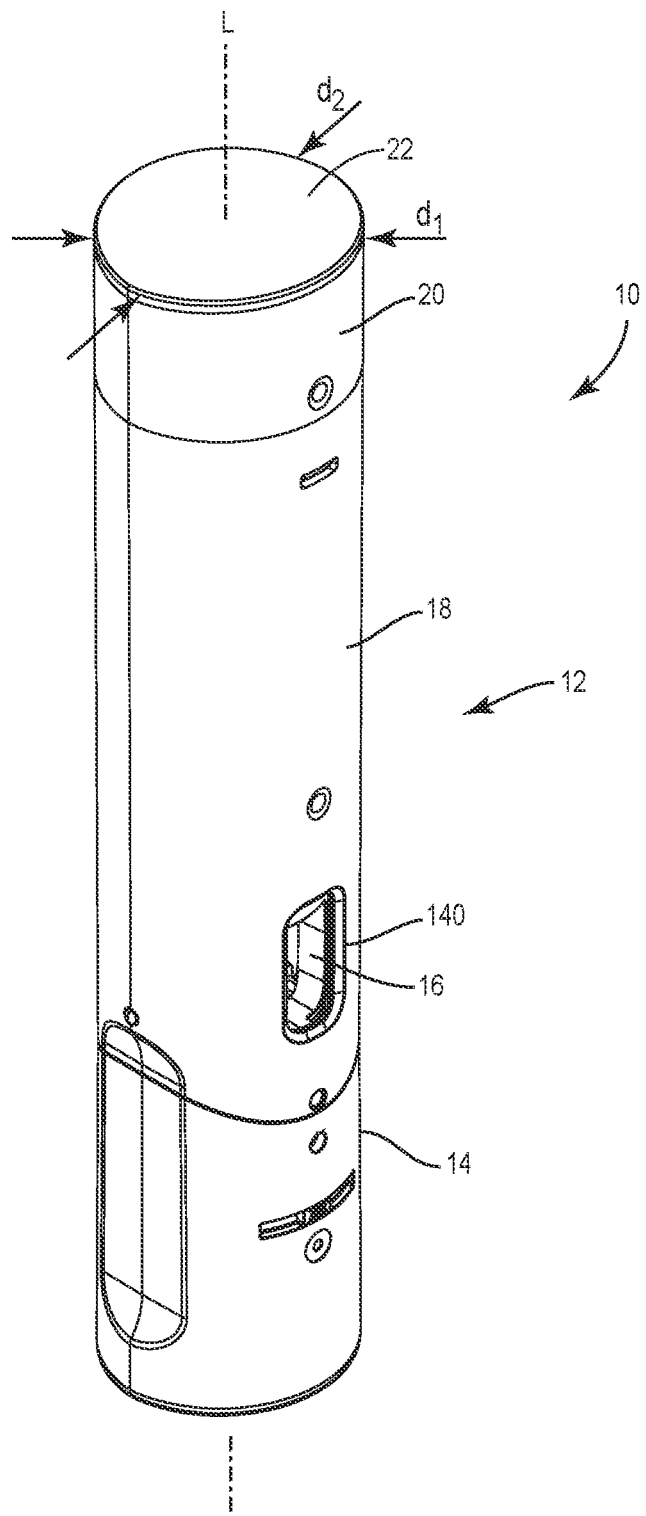
FIG. 1 is a perspective view of a device for injecting a medicament of the present disclosure, which can be an autoinjector. The device is shown assembled and capped.

Further, the relation between objects in a figure may not be to scale and may in fact have a reverse relationship as to size. The figures are intended to bring understanding and clarity to the structure of each object shown, and thus, some features may be exaggerated in order to illustrate a specific feature of a structure.

DETAILED DESCRIPTION

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. The following description is presented to enable any person skilled in the art to make and use the present disclosure.

Notwithstanding that the numerical ranges and parameters setting forth the broad scope of the application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Definitions

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", or the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

The term "medicament" includes a substance suitable for injection to treat a condition or a disease. The medicament can include an active pharmaceutical ingredient and an excipient.

The term "proximal" end of the autoinjector or device refers to the end that is closest to the patient's skin.

The term "distal" end refers to the end that is furthest from the patient's skin.

The headings below are not meant to limit the disclosure in any way; embodiments under any one heading may be used in conjunction with embodiments under any other heading.

Reference will now be made in detail to certain embodiments of the application, examples of which are illustrated in the accompanying figures. While the application will be described in conjunction with the illustrated embodiments, it will be understood that they are not intended to limit the application to those embodiments.

Device for Injecting Medicaments

New medicament delivery devices and methods are described that provide a reliable and safe injection to the user. The medicament delivery devices and methods provided allow accurate delivery of the medicament to the injection site and can be used even by untrained personnel.

The present application provides embodiments of a delivery device and related methods of use for injecting at least one dose of a medicament. The medicament can be in liquid form, such as for example, a solution, suspension, emulsion, gel, colloid, or foam.

The delivery device can be loaded with any medicament to be injected. For example, the delivery device can be loaded with one or more doses of a medicament. Suitable medicaments include, for example, an analgesic agent, an anti-inflammatory agent, a hormone, a beta agonist agent, an alpha agonist agent, a beta antagonist agent, an alpha antagonist agent, a benzodiazepine (e.g., diazepam), a glucose modulator (e.g., insulin, glucagon, dextrose), a narcotic (e.g., opioid), a narcotic antagonist (e.g., naloxone), a cholinergic agent, an anti-cholinergic agent, a muscarinic agonist agent, a muscarinic antagonist agent, a steroid, a chloride salt (e.g., potassium chloride, sodium chloride, calcium chloride), an iodide salt, a cholinesterase reactivator agent, a cholinesterase agonist, an antimicrobial agent, an anti-arrhythmic agent, a vasodilator agent, a vasoconstrictor agent, an anti-coagulant agent, a cardiovascular agent, an anti-parkinsonian agent, an anti-psychotic agent, an immunosuppressant agent, an antihistamine, selective serotonin receptor agonist, or a combination thereof. The medicament can be in liquid form, such as for example, a solution, suspension, emulsion, gel, colloid, or foam.

In some embodiments, the present delivery device includes a new emergency release pen. In some embodiments, the emergency release pen is a single use, disposable autoinjector with a pre-filled syringe. In some embodiments, the emergency release pen is configured to allow a patient to self-inject a medicament, such as for example, glucagon to treat hypoglycemia or naloxone to treat narcotic overdoses. In some embodiments, the emergency release pen is configured to be in an initial state in which a cap covers a skin sensor or needle guard of the emergency release pen. The cap is removed to expose the skin sensor. The user applies an injection force to the skin sensor, which among other things, eventually causes the plunger to move the medicament out of the container or syringe and out the needle to the injection site to deliver the medicament.

After the medicament is injected, and the needle is withdrawn from the injection site, the skin sensor then returns to the extended position to shield or cover the needle preventing further use and unwanted puncture of the skin.

The delivery device 10 shown can be a single use autoinjector 12, which is a device for injecting a medicament. In various embodiments, the needle and depth of penetration of the device can be designed for different volumes of medicine and for many types of injection. For example, in some embodiments, autoinjector 12 can be a disposable device and, in some embodiments, deliver up to 0.3 ml, and in some aspects, 0.4 ml of low viscosity formulation to an injection site having 12.7 mm to 16 mm needle injection depth. In other embodiments, the device can be designed to deliver greater or lesser volumes than those mentioned above. In many embodiments, the device can be configured for subcutaneous, intrathecal, epidural, intradermal, intramuscular, intravenous, intraperitoneal, intracardiac, intraarticular, and/or intracavernous injection. As further discussed, the insertion and withdrawal of the needle is manually driven while the injection is spring driven. The delivery device guards the needle once it has been withdrawn. The delivery device has at least a dose viewing window to allow sight of the content of the syringe or medicament container prior to operation and has additional pips or bumps on the housing to limit the risk of rolling off an inclined plane. As opposed to many conventional autoinjectors, in various aspects, the delivery device of this disclosure is activated, not by an activation or actuator button, but by a skin sensor or needle guard to prevent unwanted needle sticks.

Figure 2:
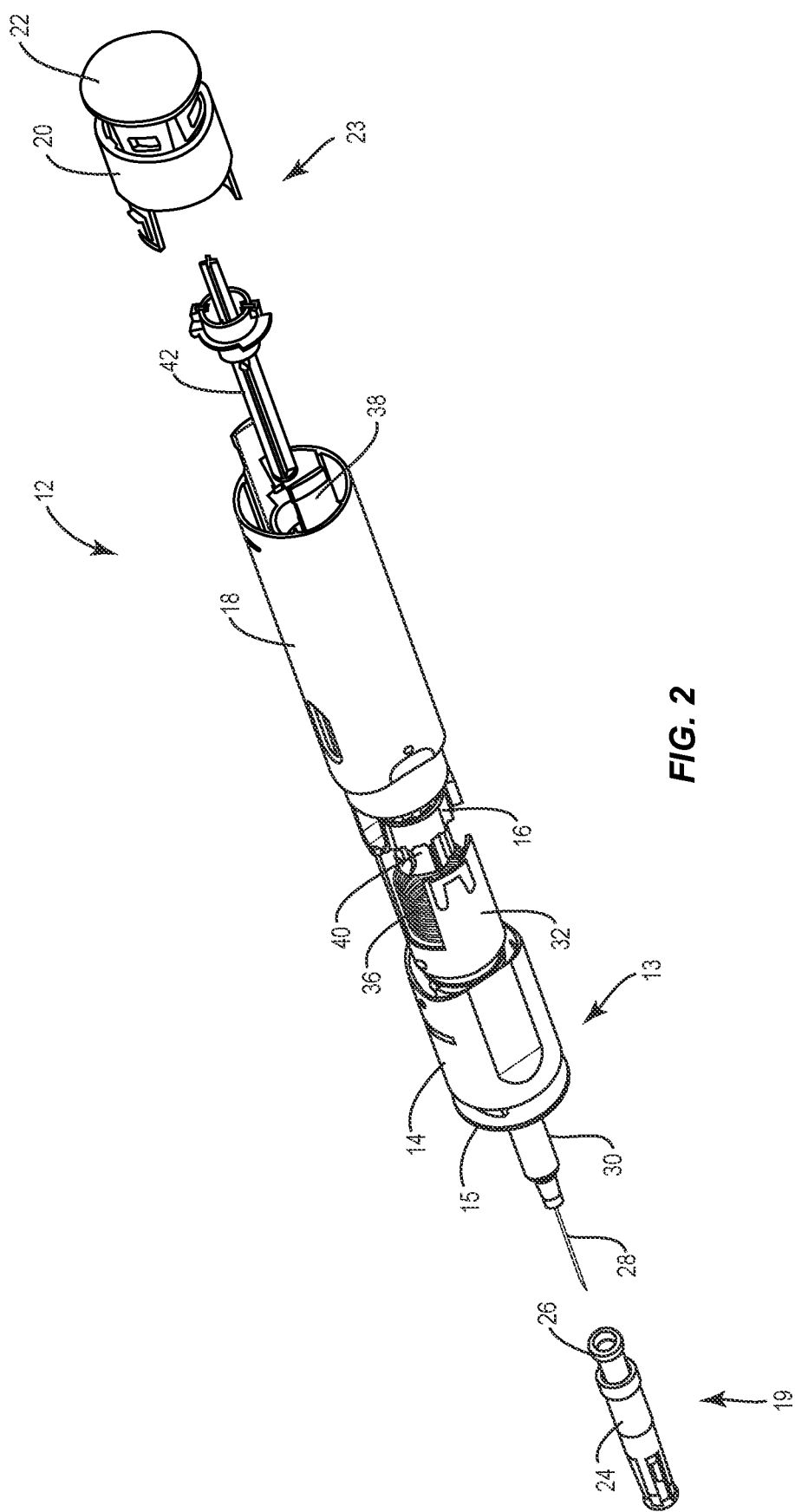
FIG. 2 is an exploded view of an embodiment of the device in FIG. 1, which can be an autoinjector.
Figure 3:
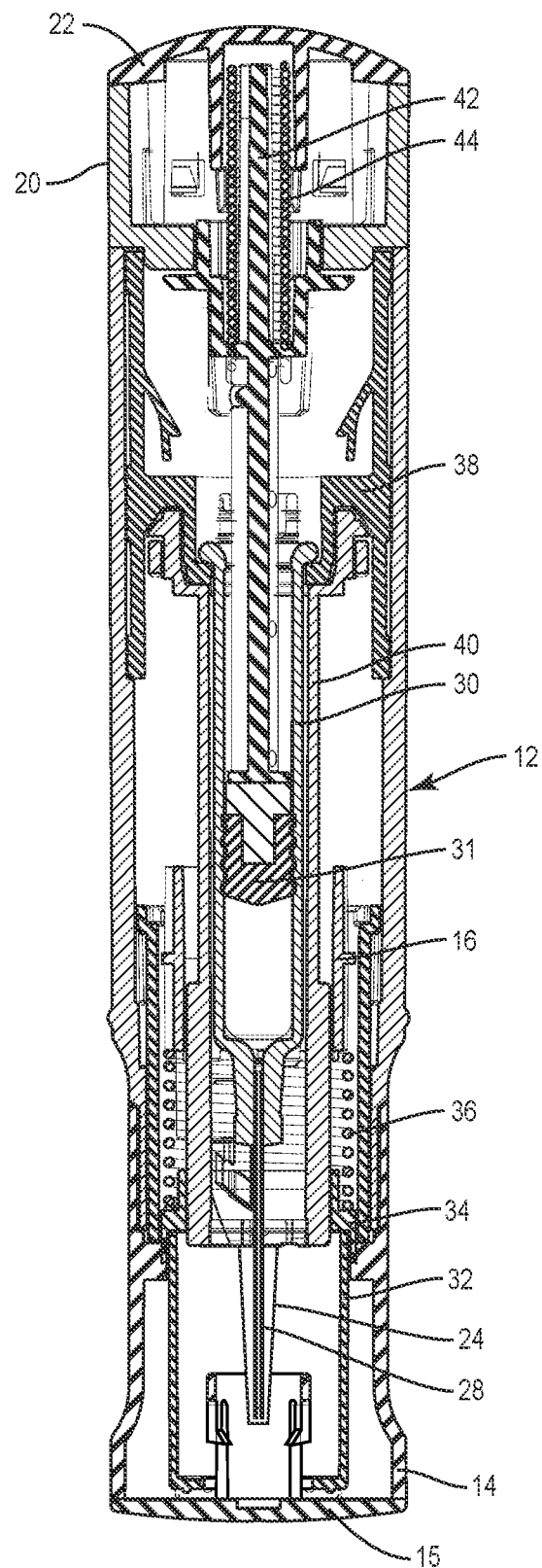
FIG. 3 is a cross sectional view of the device of FIG. 1.
Figure 4A:
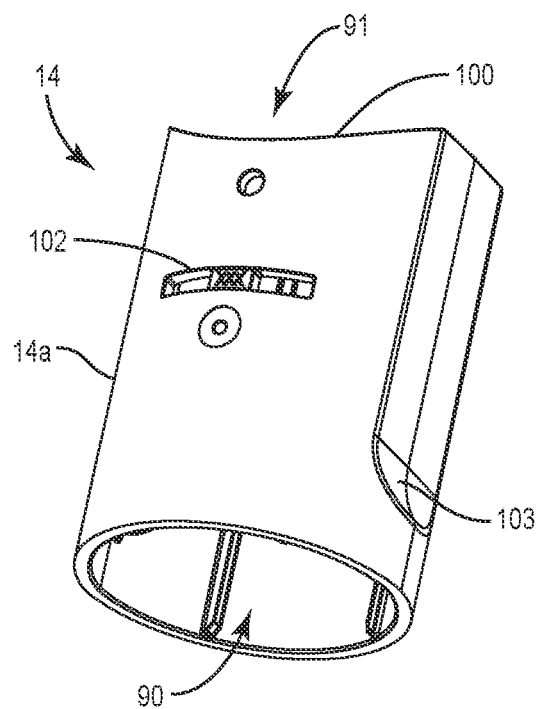
FIGS. 4A and 4B are perspective views of a removable cap of the device in FIG. 1.
Figure 4B:
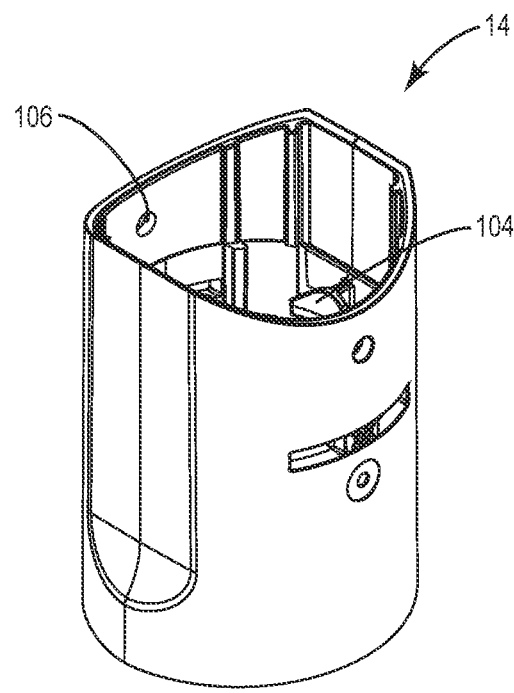
Figure 4C:
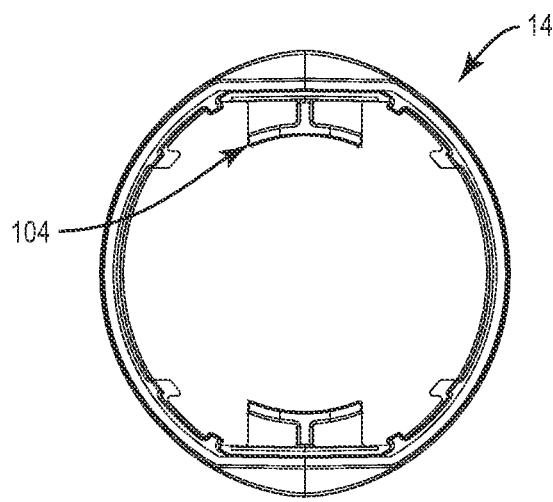
FIGS. 4C and 4D are top and bottom views, respectively, of the removable cap of FIGS. 4A and 4B.
Figure 4D:
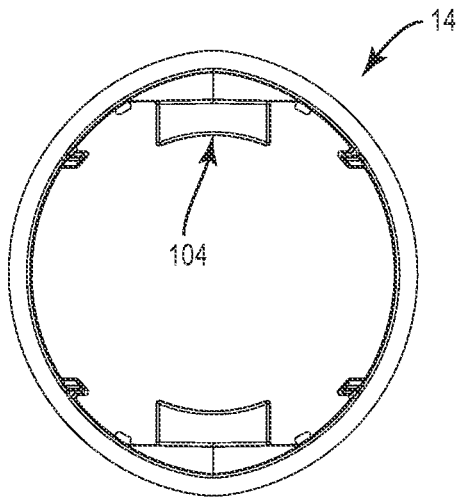
Figure 5A:
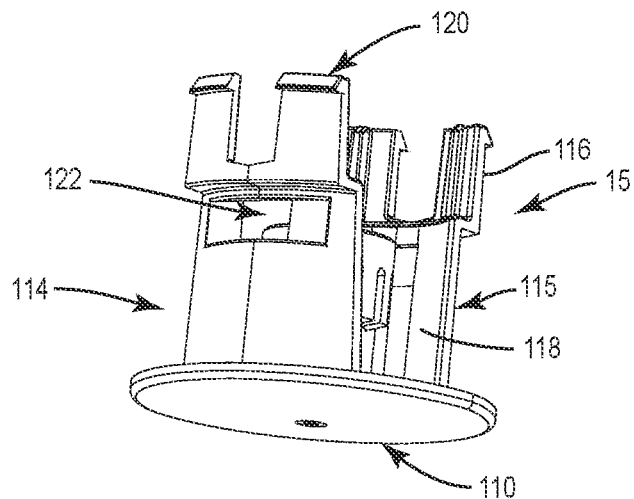
FIGS. 5A and 5B are perspective views of a cap insert of the device in FIG. 2.
Figure 5B:
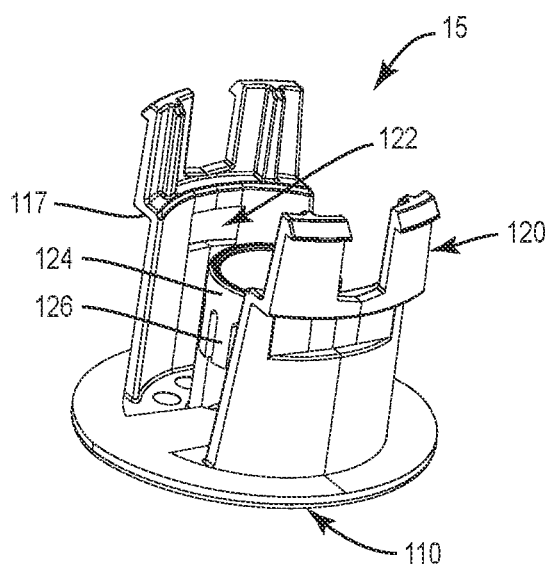
Figure 5C:
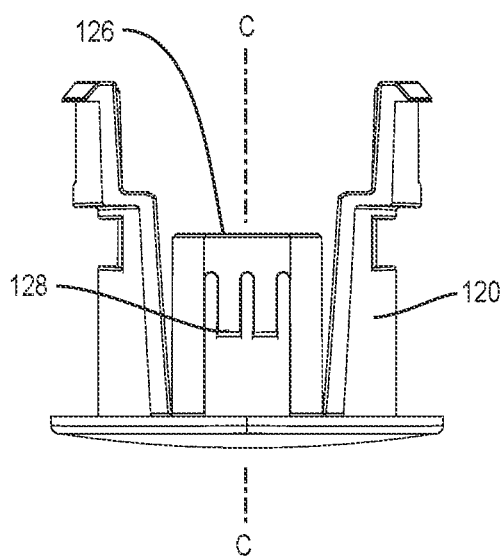
FIGS. 5C and 5D are a side view and bottom view, respectively, of the cap insert of FIGS. 5A and 5B.
Figure 5D:
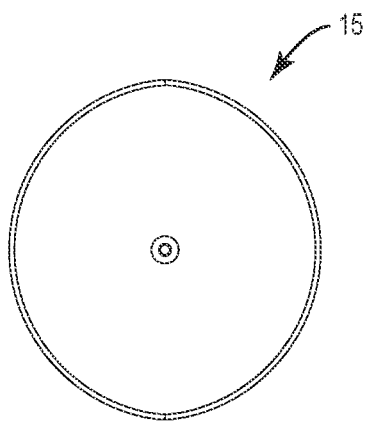
Figure 6A:
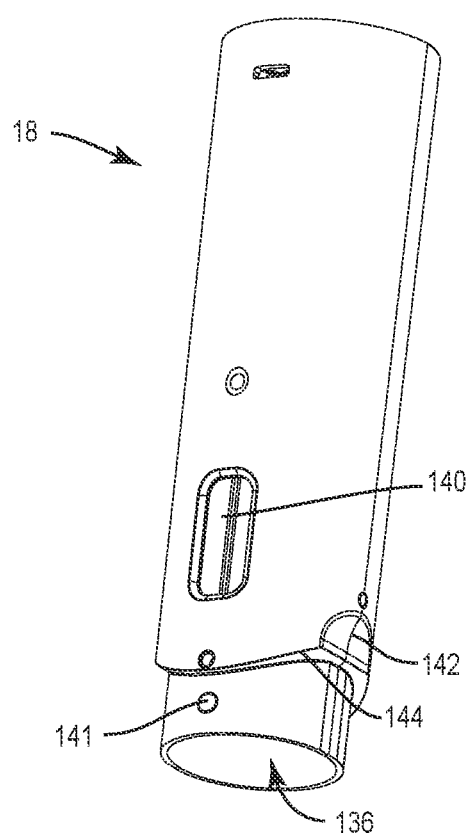
FIGS. 6A and 6B are perspective views of a housing of the device in FIG. 1.
Figure 6B:
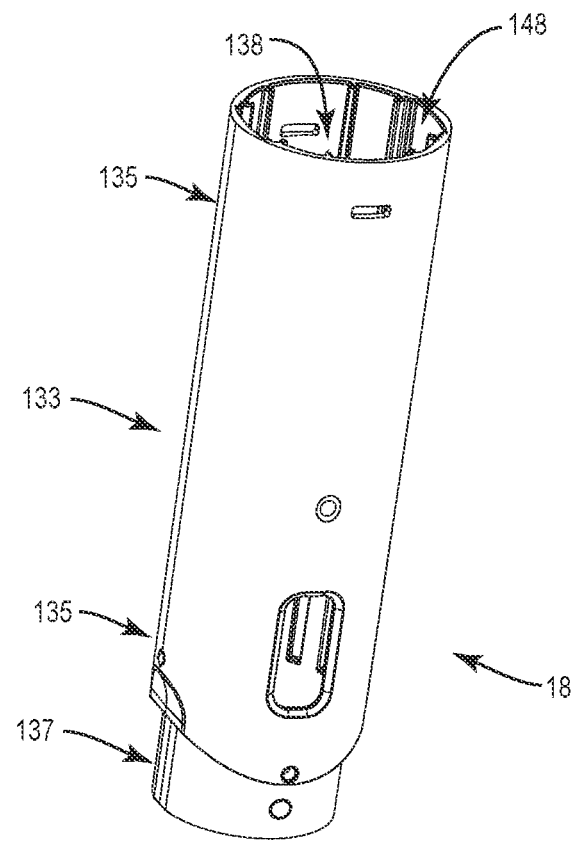
Figure 6C:
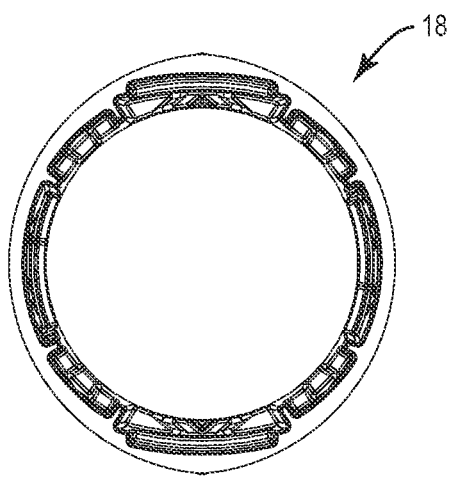
FIGS. 6C and 6D are top and bottom views, respectively, of the housing illustrated in FIGS. 6A and 6B.
Figure 6D:
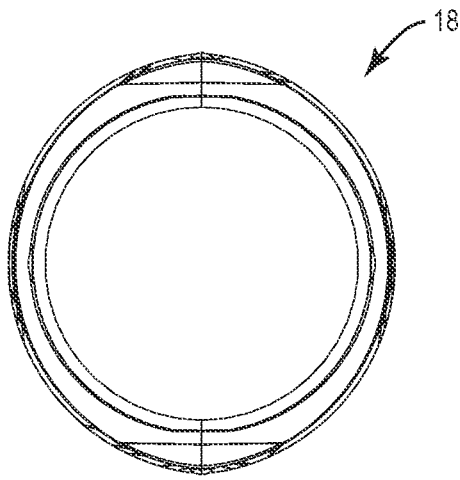
Figure 8A:
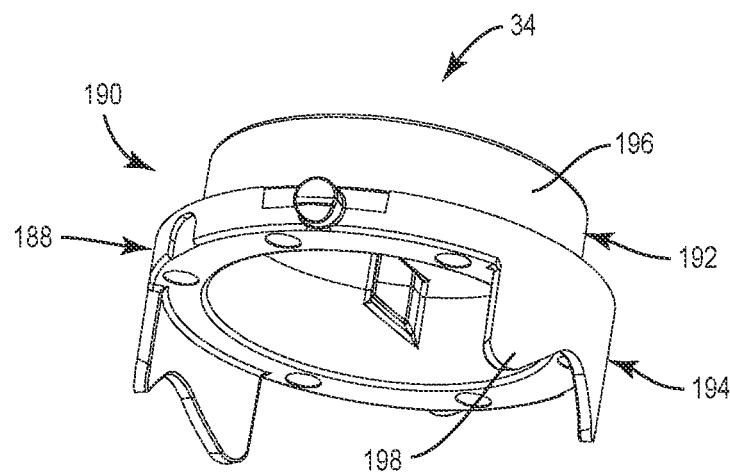
FIGS. 8A and 8B are perspective views of a skin sensor insert of the device in FIG. 3.
Figure 8B:
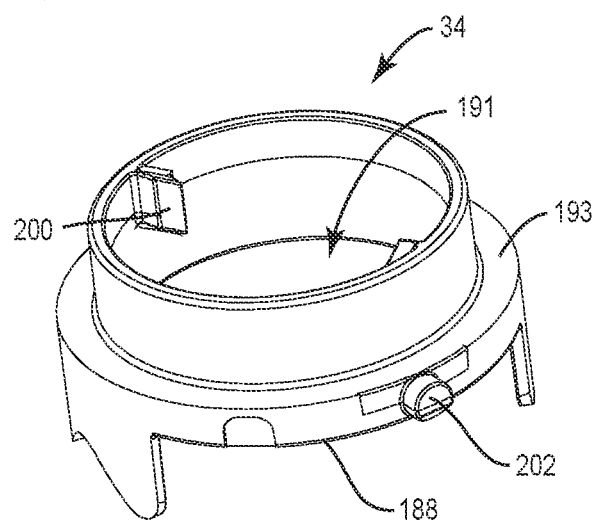
Figure 8C:
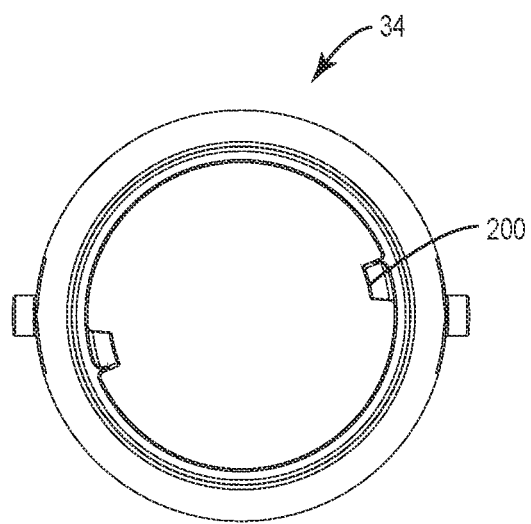
FIGS. 8C and 8D are top and bottom views, respectively, of the skin sensor insert illustrated in FIGS. 8A and 8B.
Figure 8D:
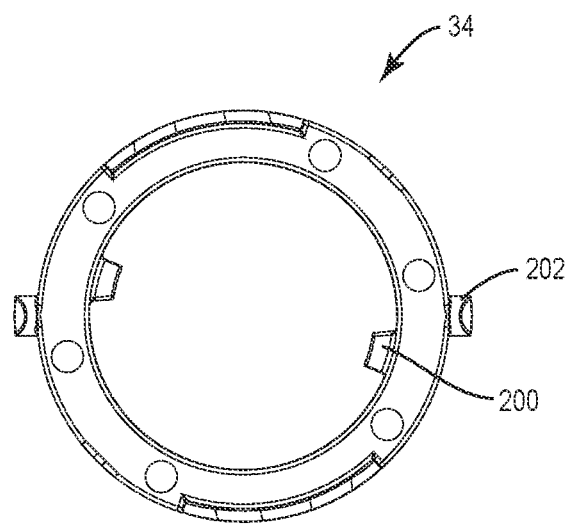

With reference to FIGS. 1-3, autoinjector 12 comprises a removable cap 14 which covers a skin sensor 32 and serves as a needle shield remover. Autoinjector 12 also includes housing 18 which is generally cylindrical along longitudinal axis LL and together with housing top 20 houses most of the other components of autoinjector 12. In some embodiments, housing 18 comprises a collar 16 which is keyed into skin sensor 32, a syringe or container 30 having a needle 28 and a syringe stopper 31 slidably located in syringe or container 30, all included at least partially in a carriage 40 configured for engagement with a plunger 42. Autoinjector 12 has a proximal end 19 and a distal end 23.

When the user removes cap 14, that action will automatically remove a needle shield 23 covering needle 28 of syringe or container 30. In some embodiments, needle shield 23 can be manufactured of a rigid material to provide a rigid needle shield 24 which protects needle 28. In other embodiments, needle shield 23 can be made of a flexible material to provide a flexible needle shield 26. In yet other embodiments, needle 28 can be protected by both a flexible needle shield 26 covered by a rigid needle shield 24. After cap 14 is removed, skin sensor 32 will not be fully extended and is partially retracted. In some embodiments, the partially retracted skin sensor 32 is a fail-safe mechanism that prevents false injection.

To inject the medicament, the user presses skin sensor 32 on the skin at the site that needs to be injected, which allows full retraction of the skin sensor toward the distal end 21 of a carriage 40, the skin sensor will engage a skin sensor spring 36, which will engage a collar 16 without the collar rotating. Collar 16 will engage a carriage 40 and cause the carriage to rotate once the needle 28 has been inserted to the specified depth. The rotation of carriage 40 will cause the rotation of a plunger 42 disposed at the distal end 21 of carriage 40. The distal end of the carriage has slots/holes that allow the plunger 42 to extend after carriage 40 is rotated fully to the position that allows the plunger 42 to pass through via a channel present in the carriage.

In some embodiments, autoinjector 12 includes a cap 14 configured to cover skin sensor 32 when autoinjector 12 is in a storage state. One embodiment of cap 14 is shown in FIGS. 4A-4D. In this embodiment, cap 14 has a generally elongate tubular shape body 14a open at both ends with a generally oval cross-sectional profile. The major axis $d_1$ of the oval profile is about 28 mm and the minor axis $d_2$ is about 25 mm. At the proximal end, cap 14 has proximal opening 90 adapted to receive cap insert 15 and clip recesses 102 which provide positive clip retention between cap 14 and cap insert 15. Opposite proximal opening 90, cap 14 has distal opening 91 adapted to connect to housing 18 through a profiled interface 100 that facilitates cap removal from housing 18 by providing a natural lead out and therefore provide tension on the label when the cap is twisted off. Externally, cap 14 contains grip features 103 which facilitate holding the cap. Internally, cap 14 contains lock actuation lugs or cams 104 for providing a locking method for the autoinjector to be activated when cap 14 is fitted and a skin sensor insert 34 is in a locked position. Cap 14 also contains a retention hole 106 which interacts with a soft location bump on housing 18 thereby enhancing cap retention. The length of the tubular shape body 14a from the proximal end to retention hole 106 is about 30 mm.

A cap insert 15 is coupled to cap 14 to cover opening 90 that extends through a proximal end of cap 14. One embodiment of cap insert 15 is shown in FIGS. 5A-5D. In this embodiment, cap insert 15 comprises a flat cover 110 and a cap insert body 114. Flat cover 110 has a substantially oval shape of similar size as the oval cross-sectional profile of cap 14. Flat cover 110 comprises a rigid and/or flexible needle shield capture member 124 which is centrally disposed on the circular flat cover 110 projecting in the distal direction. In some aspects, the rigid and/or flexible needle shield capture member 124 is shaped as a tubular shaft 126 having clip hooks 128 configured for engaging with the end flanges 27 of the rigid needle shield 24 and removing it when cap 14 is removed. Capture member 124 has a length of about 10 mm and an outside diameter of about 8 mm. In various aspects, cap insert body 114 has two arms 115 having opposed inner concave surfaces and disposed around needle shield capture member 124, extending longitudinally along axis CC and spaced apart from one another. Each arm 115 has an upper body 116 and a lower body 118 abutting upper body 116. Upper body 116 of arms 115 includes a base 117 from which clip features 120 extend distally along longitudinal axis CC for providing a positive clip retention between cap 14 and cap insert 15. In another embodiment, each clip feature 120 has two arms extending from base 117 forming a U shape therebetween. Lower body 118 of arms 115 includes clip apertures 122 to provide a positive feature to clip to skin sensor 32.

Figure 18C:
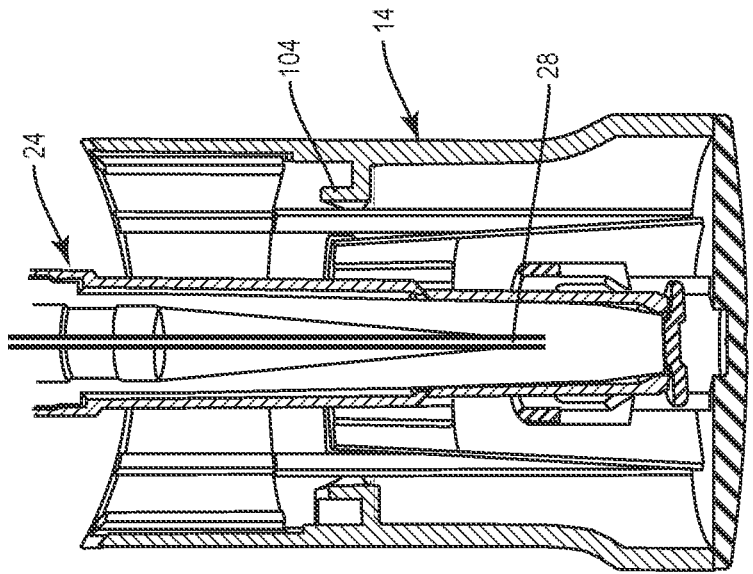
FIG. 18C is a cross sectional view of the interaction between cap and rigid needle shield of an embodiment of the device in FIG. 3.
Figure 18B:
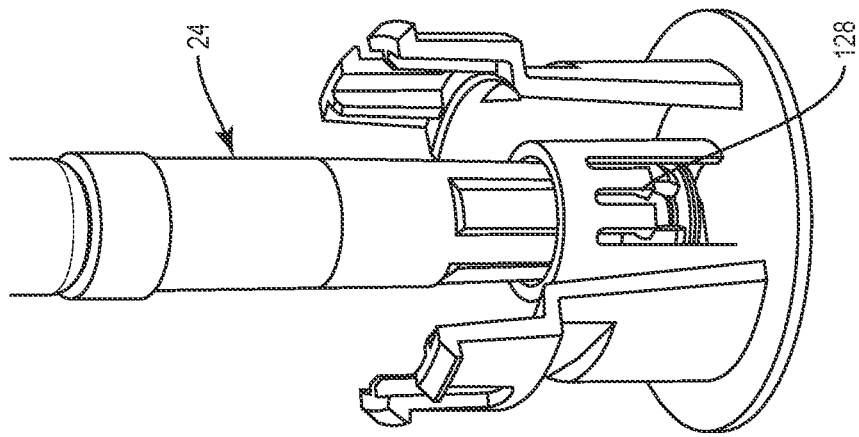
FIGS. 18A and 18B are perspective views of the interaction between cap and rigid needle shield of an embodiment of the device in FIG. 3.
Figure 18A:
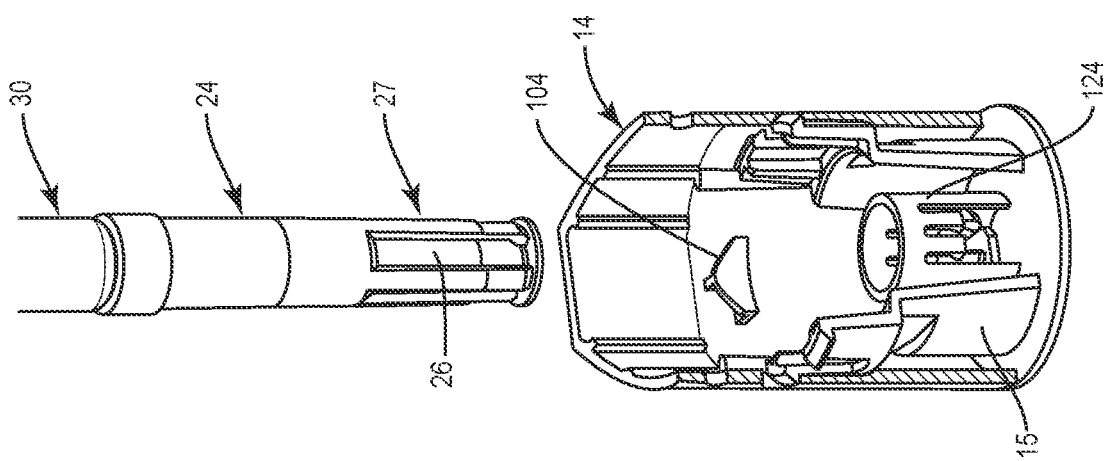

In some embodiments, syringe or container 30 is protected by a flexible needle shield 26 that is coupled to a rigid needle shield (RNS) 24, as shown in FIGS. 2 and 18a, for example. Flexible needle shield 26 envelopes needle 28 and is surrounded by rigid needle shield 24, both configured to protect a needle 28 of syringe or container 30. Rigid needle shield 24 comprises a cylindrical shape tapered surface at the tip of needle 28 and having end flanges 27 for interacting with clip hooks 128 of the tubular shaft 126 of cap insert 15. On the removal of cap 14, clip hooks 128 catch on to the end flanges 27 of rigid needle shield 24 to remove it from syringe or container 30. In some aspects, clip hooks 128 of cap insert 15 can remove flexible needle shield 26 and rigid needle shield 24 simultaneously when the cap assembly of cap 14 and cap insert 15 is removed. In some embodiments, rigid needle shield 24 can have a length of from about 25 mm to about 35 mm and an outside diameter at its distal end of about 5 mm.

To initiate the operation of autoinjector 12, the user removes cap 14 by pulling and/or twisting. This action can cause three key actions: (i) the label that is fixed to both the autoinjector body and cap 14 is torn in two; (ii) rigid needle shield 24 is pulled off from within autoinjector 12; and (iii) the skin sensor lock that secures the autoinjector during carriage is released. The device label is intended to be attached to both the device body and the cap, so removal of the cap tears the label along a profiled line of perforations and thus provides tamper-evidence of use, and of breaking of sterility.

The cap assembly (cap 14 and cap insert 15), is clipped on to end flanges 27 of the rigid needle shield (RNS) 24 during assembly, so that when cap 14 is removed, the RNS is pulled off the syringe at the same time. Thus, when the cap is removed, the needle shield is also removed.

With reference to FIGS. 6A-6D, in one embodiment, housing 18 has a generally elongate tubular shaped body open at both ends with a generally oval cross-sectional profile of substantially the same size as that of removable cap 14. The tubular shaped body 133 of housing 18 comprises a lower part 134, an upper part 135 and two openings, proximal opening 136 and distal opening 138. In some embodiments, the tubular shaped body 133 of housing 18 is monolithic. At the proximal end, lower part 134 has proximal opening 136 having a substantially round circumference and a substantially cylindrical portion 137 configured to fit into the cap assembly. In some embodiments, at the proximal opening 136, lower part 134 has an outside diameter of about 20 mm. At its distal end, lower part 134 has a profiled interface 144 adjacent upper part 135 for providing a natural lead out to cap 14. Cylindrical portion 137 contains two pips 141 spaced apart from one another and configured to provide a natural fit with the retention holes 106 of cap 14. The tubular shape body 133 of housing 18 also contains grip features 142 positioned to continue with grip features 103 of cap 14 to provide for smooth gripping portions for autoinjector 12 prior to use.

The housing may be of various shapes including, but not limited to, cylindrical, round, or rectangular. The housing may have contours and allow easy grasping of the device during use. In some embodiments, the housing can be angled for right and left hand users or can be generic for both hands.

To provide improved visibility of the syringe and its contents, in the tubular shape body of housing 18 there can be at least two windows 140 disposed above cylindrical portion 137 spaced apart from one another. Window 140 is configured to allow visualization of a material, such as, for example, a syringe or container 30 and/or a medicament within syringe or container 30. In one embodiment, window 140 is configured to be a first color, such as, for example, red when there is no syringe and/or medicament within housing 18 and a second color, such as, for example, green when there is a syringe and/or medicament within housing 18. Housing 18 further includes grip feature 142 which mates with grip feature 103 of cap 14. Housing 18 also includes a profiled cap interface 144 which also mates with cap 14 to provide a natural lead out and tension when cap 14 is twisted off. To provide for a positive retention of skin sensor 32 and eliminate the potential for removal of the skin sensor after use, housing 18 includes at least two (2) skin sensor slots 148. Below each window 140, the tubular shape body of housing 18 contains an assembly hole 150 provided to enable a secure retention of skin sensor 32 when the cap assembly is being fitted during an automated assembly of the autoinjector. In some embodiments, the overall length of tubular shaped body 133 of housing 18 is about 90 mm.

Other elements of an autoinjector included in housing 18 comprise skin sensor 32 which includes a skin sensor insert 34, a skin sensor spring 36, a carriage 40, a collar 16, constrainer 38, a carriage thrust bearing 41, a plunger 42, plunger spring 44, housing top 20 and housing top insert 22, all interacting with each other as described herein.

A skin sensor 32 is disposed in housing 18. An end of skin sensor 32 is configured for engagement with tissue, such as, for example, skin when autoinjector 12 injects a material, for example, a medicament, into or beneath the skin of a patient. One embodiment of skin sensor 32 is shown in FIGS. 7A-7D. With reference to FIGS. 7A and 7B, skin sensor 32 comprises a body 170 having a lower tubular portion 172 proximally located, a distally located upper tubular portion 174 and a bore 161 throughout body 170. At the proximal end, bore 161 is bordered by a front face 171 of tubular lower portion 172, wherein front face 171 has a central aperture 173 configured to allow needle 28 to move through once the autoinjector 12 is pressed against an injection site and the skin sensor is retracted.

By comparison to the distally located upper tubular portion 174, the tubular lower portion 172 has a reduced diameter profile which is adapted to allow skin sensor insert 34 to incorporate a locking mechanism. In some embodiments, the diameter of lower portion 172 is about 15 mm. Externally, lower tubular portion 172 also comprises at least two cap subassembly retention pips 164 spaced apart from one another which facilitate the clipping of cap 14 subassembly to skin sensor 32. Upper tubular portion 174 of skin sensor body 170 comprises a base 175 abutting lower portion 172 and two arms 176 which extend generally axially from base 175 along longitudinal axis DD and have opposed inner concave surfaces adapted to receive skin sensor spring 36. Upper tubular portion 174 of skin sensor 32 includes at least a clip slot 160 configured to receive at least an external lug 196 of the skin sensor insert 34. In some embodiments, upper tubular portion 174 has two clip slots 160 configured to receive external lugs 196 of skin sensor insert 34. Each arm 176 includes an external lug 162 having a double dovetail section which provides a positive location within housing 18 to ensure function and to eliminate the potential for removal of the skin sensor 32 after use. In some aspects, the diameter of the upper tubular portion 174 of skin sensor 32 is about 20 mm. In other aspects, the overall length of skin sensor 32 is about 57 mm.

Upper tubular portion 174 of skin sensor 32 also includes a skin sensor cam or ramp 166 which, in some aspects, can interact with exterior tabs 62 of collar 16 to overcome an initial threshold force generated by the interaction of end face 171 of the skin sensor 32 with the skin of a user. Upper tubular portion 174 of skin sensor 32 further includes an assembly relief feature 167 added to its skin sensor base 175 which provides location and a clip form when assembling the skin sensor insert 34. In addition, assembly relief feature 167 can provide assembly assistance and causes the skin sensor insert 34 to lock to carriage 40 while the two components are fastened together.

A skin sensor insert 34 is disposed within skin sensor 32. One embodiment of the skin sensor insert 34 is illustrated in FIGS. 8A-8D. With reference to FIGS. 8A-8D, skin sensor insert 34 comprises a tubular body 190 which has a cylindrical distally located upper body 192 defining a bore 191 and abutting a proximally located lower cylindrically shaped skirt 194 having a base 188 and a face 193 extending generally radially outwardly from upper body 192 and perpendicular to base 188. In various embodiments, the diameter of upper body 192 is about 14 mm. In some embodiments, the diameter of base 188 is about 17 mm. Skirt 194 comprises a pair of actuation wings or W shaped cams 198 which extend generally axially from base 188 to provide means for the cap assembly to interact with skin sensor insert 34 and rotationally drive pins 200 into a locked position. In some embodiments, externally, upper body 192 comprises a spring alignment boss 196 which reduces the risk in eliminating potential spring end catching and provides compensation for increase in the length of the skin sensor spring 36. An embodiment of skin sensor spring is illustrated in FIG. 16*a*. Internally, upper body 192 further comprises pin 200 required to enable a desired locking function of sliding up an angled face of the carriage for a locking mechanism as further described in this disclosure. Skirt 194 comprises an external retaining pin 202 which retains skin sensor insert 34 into the skin sensor and provides freedom to rotate as required for a locking mechanism.

Figure 9A:
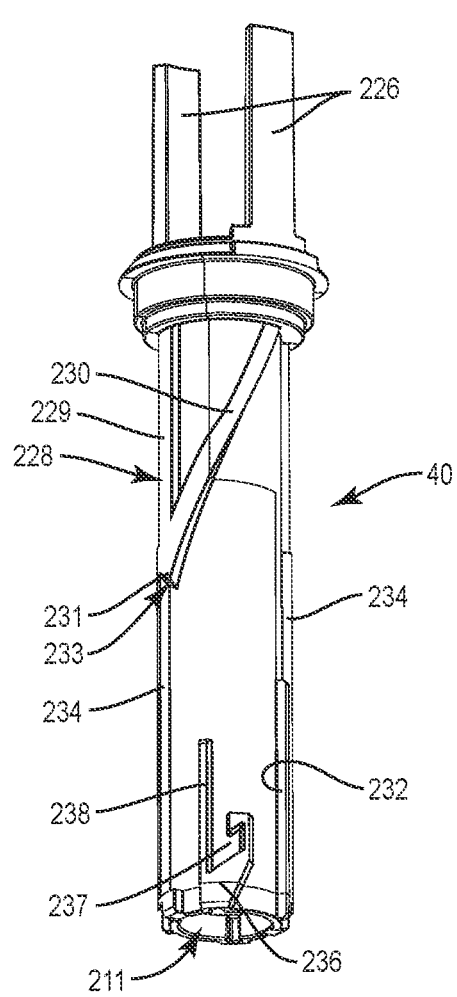
FIGS. 9A and 9B are perspective views of a carriage of the device in FIG. 2.
Figure 9B:
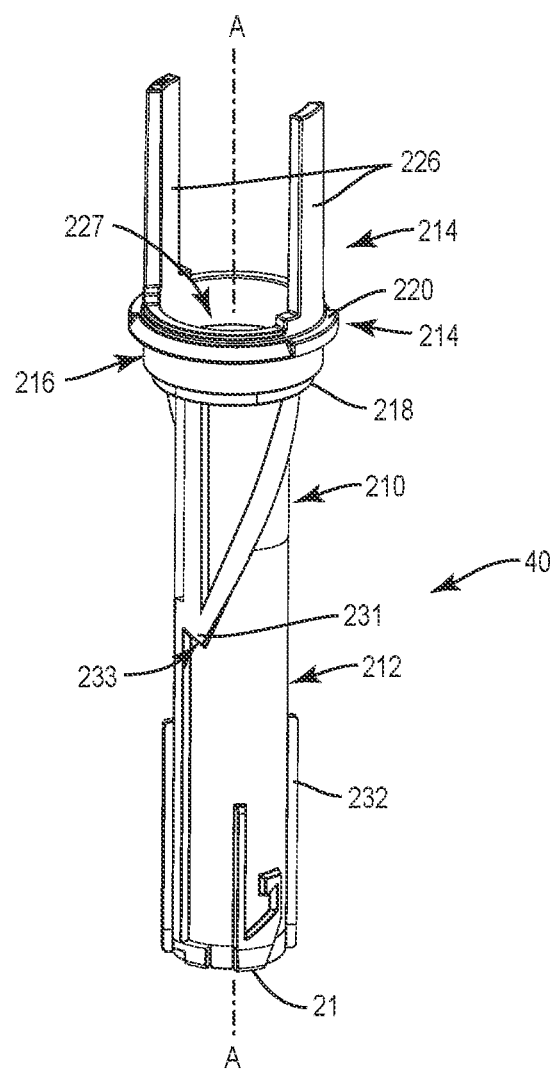

Housing 18 further includes a carriage 40 and a collar 16 configured to be slidably positioned over carriage 40. One embodiment of carriage 40 is shown in FIGS. 9A-9B.

Carriage 40 has a tubular shaped body 210 along longitudinal axis AA, the tubular shaped body having a lower portion 212 and an upper portion 214 abutting lower portion 212. In one aspect, carriage 40 is monolithic and manufactured from transparent material. Lower portion 212 has a proximal opening 211. In some aspects, the outside diameter of lower portion 212 is about 10 mm. Externally, lower portion 212 comprises at least one ramp ridge 228 and, in some embodiments, two ramp ridges 228 spaced apart from one another, in some aspects, on opposite sides of lower portion 212 and disposed at the distal end of lower portion 212. Ramp ridge 228 has a straight edge 229 and an arcuate edge 230 which meet at a point 231 and provide a carriage threshold face 233 which is configured to receive collar 16 so that the collar which cooperates with skin sensor 32 can partially rotate carriage 40. Skin sensor 32 effects a precompression on spring 36, which pre-compression force acts axially on collar 16 which causes a turning moment on carriage 40 by means of arcuate edge 230. In some embodiments, arcuate edge 230 can be helical. In various aspects, straight edge 229 can have a length of about 25 mm and arcuate edge 230 can have a length of about 30 mm.

In various embodiments, lower portion 212 comprises at least an abort rib or rail 232, an injection rail or rib 234 spaced apart from one another and an inverted J rib or lock rail 236, all disposed around proximal opening 211 of carriage body 210 and are included for the needle insertion and abort functions, and injection functions available to autoinjector 12. Abort rib or rail 232 and injection rib or rail 234 are spaced apart from one another but arranged next to each other with the abort rib shorter than the injection rib. In various embodiments, injection rail 234 abuts straight edge 229 of ramp ridge 228. In some aspects, abort rail 232 has a length of about 20 mm and injection rail has a length of about 36 mm. Abort rib 232 is positioned between inverted J rib or rail 236 and injection rail 234. Inverted J rib 236 has a straight side 238 and a U-shaped channel 237. In various aspects, the straight side 238 of inverted J rail 236 has a length of about 16 mm. In other aspects, all external rails of carriage 40 have a thickness of about 1.5 mm. In some embodiments, abort rib 232, injection rib 234 and inverted J rib or lock rail 236 include a pair each that are spaced apart and facing one another.

In other embodiments, upper portion 214 comprises a base 216 that has a lower rim 218 and upper rim 220, both rims configured to receive a carriage thrust bearing 41. In some embodiments, upper portion 214 of carriage 40 further comprises two arms or ears 226 extending from upper rim 220 positioned around distal opening 227, facing each other and creating a U shape with upper rim 220. In various embodiments, lower rim 218 has an outside diameter of about 10 mm and upper rim 20 has an outside diameter of about 17 mm. In other embodiments, arms or ears 226 have a length of about 21 mm.

Figure 10A:
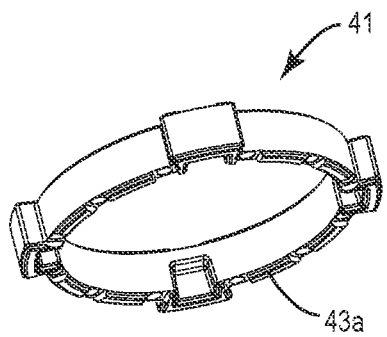
FIGS. 10A and 10B are perspective views of a carriage thrust bearing of the device in FIG. 2.
Figure 10B:
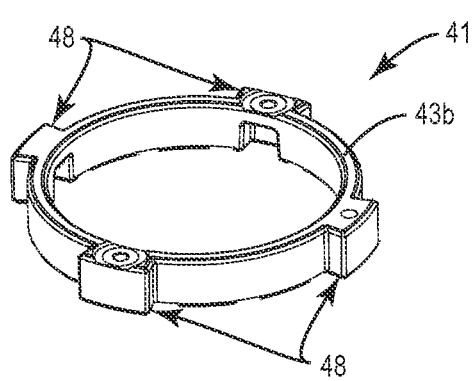
Figure 11A:
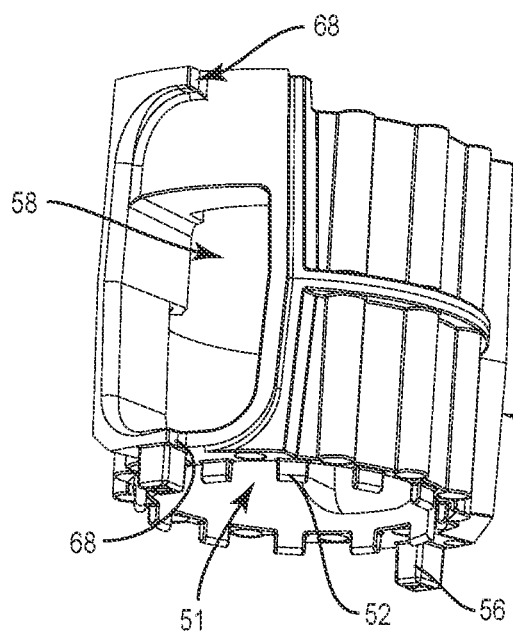
FIGS. 11A and 11B are perspective views of a collar of the device in FIG. 2.
Figure 11B:
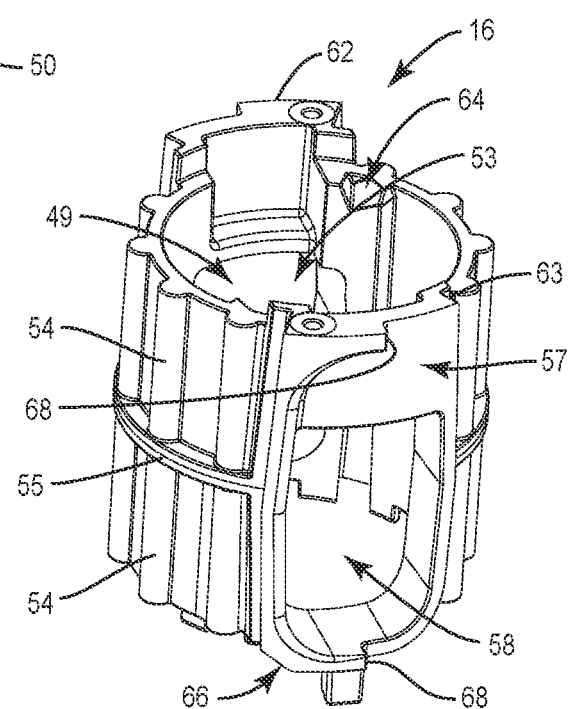
Figure 11C:
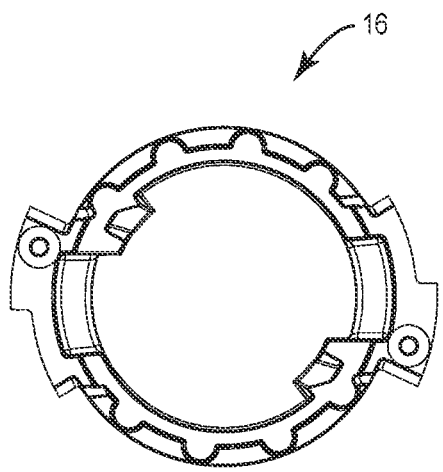
FIGS. 11C and 11D are top and bottom views, respectively, of the collar illustrated in FIGS. 11A and 11B.
Figure 11D:
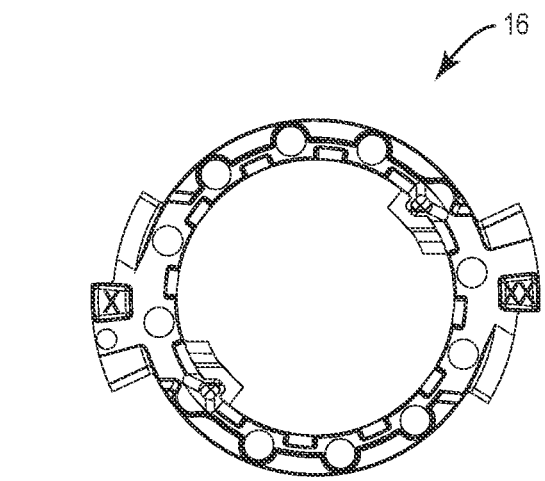

A collar 16 is coupled at the proximal end to skin sensor 32 and, at the distal end, to carriage 40. One embodiment of collar 16 is illustrated in FIGS. 11A-11D. In this embodiment, collar 16 has a tubular body 50 having a bore 49 therethrough, body 50 being defined by a ribbed wall which has a proximal opening 51 and a distal opening 53 and is configured to slide over carriage 40. Externally, collar 16 comprises ribs 54 and ridges 55, both useful for ejector optimization and to provide enough wall thickness. In one embodiment, ribs 54 have a length of about 17 mm. At the distal end, tubular body 50 has collar threshold face 64 configured to couple with carriage threshold face 233 under the loading of skin sensor spring 36. In one embodiment, carriage thrust bearing 41 is illustrated in FIGS. 10A and 10B. Carriage thrust bearing 41 has a proximal surface or lower face 43a, a distal surface or upper face 43b and four tabs 48. Surface 43a of the four tabs 48 contacts the bottom of slots in housing 18 that define where carriage thrust bearing 41 is located axially in housing 18. Distal surface 43b contacts the underside of upper rim 220 of carriage 40. In some embodiments, the outside diameter of carriage thrust bearing 41 is about 20 mm.

At the proximal end, tubular body 50 of collar 16 includes spring alignment bosses 52. In various embodiments, bosses 52 surround proximal opening 51, are spaced apart from one another and configured to eliminate potential end catching of skin sensor spring 36, which is coupled to collar 16. Tubular body 50 of collar 16 contains two windows 58 spaced apart from an facing one another, each window being framed by a flag area 57 provided as an indicator to patients when autoinjector 12 is in use. In some aspects, the length of window 58 is about 17 mm, and when window 58 is of rectangular shape, the width is about 7 mm. In several embodiments, collar 16 is manufactured in a green color to serve as a patient indicator of the status of the autoinjector. Tubular body 50 also includes assembly features 56 located at its proximal end below each window aperture 58. In some embodiments, at the distal end of tube 50, collar 16 includes exterior tabs 62 that are movably disposed in slots of housing 18 to key collar 16 to housing 18 rotationally.

Figure 12A:
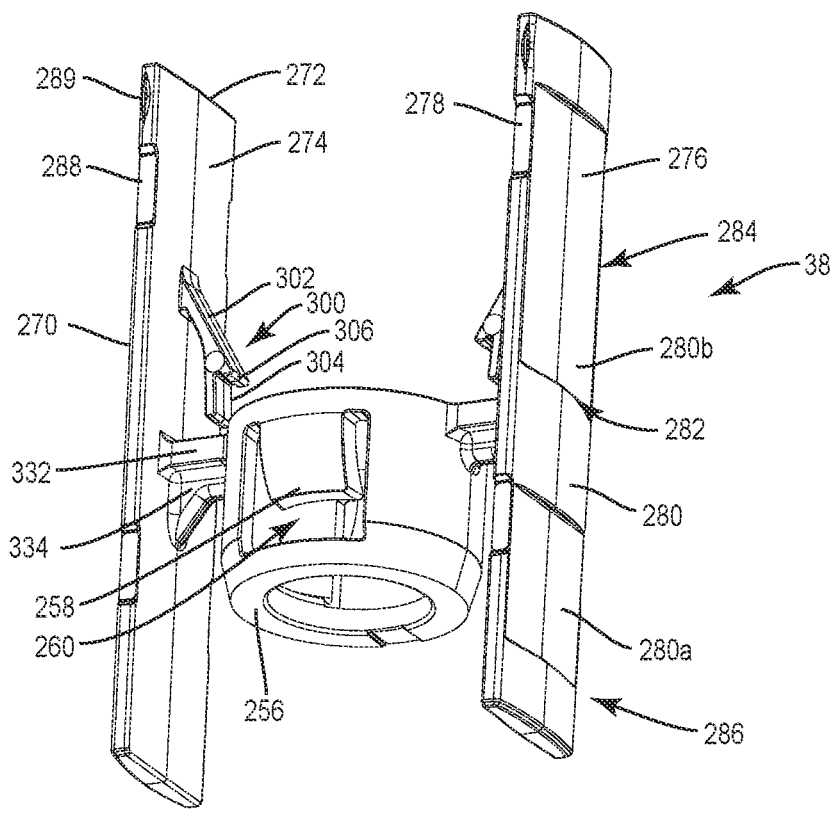
FIGS. 12A and 12B are perspective views of a constrainer of the device in FIG. 2.
Figure 12B:
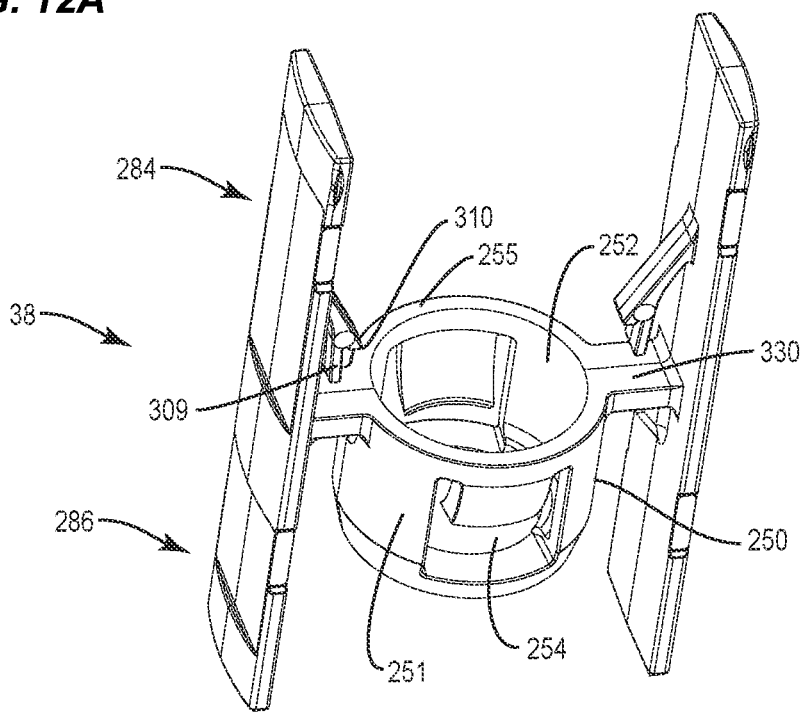

The position of syringe or container 30 is further controlled by a constrainer 38. In some embodiments, constrainer 38 is configured to suspend syringe or container 30 in the center of carriage 40 thereby transmitting the needle injection loads into housing 18. One embodiment of constrainer 38 is illustrated in FIGS. 12A-12B. In this embodiment, constrainer 38 comprises a cylindrical body 250, a wing member 270 adjacent to body 250 and extending along longitudinal axis BB and a bridge member 330 which connects cylindrical body 250 to wing member 270. In some embodiments, cylindrical body 250 is supported by two bridge members 330 between two wing members 270.

Cylindrical body 250 is defined by a circumferential wall 251, a distal opening 252 and opposite to it, a proximal opening 254. At the proximal end, constrainer body 250 has a flat face 256 that contacts syringe or container 30 and at the distal end, cylindrical body 250 has a rim 255.

In various embodiments, in circumferential wall 251, constrainer body 250 contains a syringe retaining clip 258 attached to rim 255. In some aspects, the outside diameter of constrainer body 250 is about 14 mm. Surrounding retaining clip 258 is a substantially rectangular cutout 260, which together with retaining clip 258 is configured to secure syringe or container 30 suspended in center of carriage 40.

In some aspects, retaining clip 258 has a rectangular shape formed as a tapered or arcuate tab extending toward an inner surface of the constrainer body 250. In some aspects, cutout 260 forms a U shape around a slightly concave retaining clip 258.

In various aspects, constrainer 38 includes a wing member 270, in some aspects two wings 270 spaced apart from one another and connected to constrainer body 250 by bridge member 330. In some aspects, wing member 270 has a rectangular body 272 comprising a first surface 274, a second surface 276 and a side surface 278 between the first and second surfaces. In other aspects, the length of wing member 270 can be about 40 mm. First surface 274 can contain a feedback arm 300 and bridge member 330. In other aspects, second surface 276 can contain grooves 280 and ridges 282. Side surface 278 can also contain grooves 288 and ridges 289.

In various embodiments, bridge member 330 bisects body 272 of wing members 270 defining an upper wing portion 284 above constrainer body 250 and a lower wing portion 286 below constrainer body 250. In some aspects, upper wing portion 284 is longer than lower wing portion 286. In other aspects, upper wing portion 284 can have a length of about 22 mm and lower wing portion 286 can have a length of about 17 mm. Grooves 280a on second surface 276 of upper wing portion 284 are larger than grooves 280b on second surface 276 of lower wing portion 286. In some aspects, wing member 270 contains at least two grooves.

In various aspects, bridge member 330 comprises a rectangular arm 332 and a triangular support 334 disposed below and abutting rectangular arm 332. Triangular support 334 has a triangular surface that can depress lightly and more contact points to wing member body 272 than constrainer body 250.

In some aspects, feedback arm 300 comprises an upper arm 302, a lower arm 304 and an elbow joint 306 connecting the upper arm 302 and the lower arm 304. Upper arm 302 comprises a first end adjacent to first surface 274 of upper wing portion 284 and a second end 309 having a tip 310 that protrudes slightly over elbow joint 306 forming an L shape with lower arm 304, the lower arm being longer than tip 310. In other aspects, upper arm 302 and lower arm 304 extend toward constrainer body 250 and form a U-shape with upper wing portion 284. In some aspects constrainer 38 is monolithic. In various aspects, upper arm 302 can have a length of about 6 mm and lower arm 304 can have a length of about 2 mm.

In various embodiments, constrainer 38 is configured to produce an audible sound and/or a tactile feedback in order to indicate that plunger 42 has been activated to push the medicament inside syringe or container 30 when the plunger 42 contacts elbow joint 306 of feedback arms 300. In various embodiments, container 30 does not move longitudinally relative to housing 18.

Syringe 30 includes a stopper 31 movably positioned therein, as shown in FIG. 3, for example. One embodiment of syringe or container 30 is illustrated in FIGS. 17A and 17B. In the embodiment of FIG. 17B, syringe or container 30 contains medicament 29. One embodiment of stopper 31 is shown in FIGS. 17C and 17D. In various embodiments, stopper 31 is configured for engagement with a plunger 42 to move stopper 31 within syringe or container 30 to expel a medicament from syringe or container 30. Syringe or container 30 further comprises needle 28. In various embodiments, depending upon the location of the injection, the length of needle 28 can vary from about ⅞ of an inch to about 1 inch and having a gauge from about 25 to about 27

G, from about ⅞ of an inch to about 1¼ inches and having a gauge of from about 22 to about 25 G, and from about 1 inch to about 1½ inches and having a gauge of from about 19 to about 25 G.

Plunger 42 extends through constrainer 38 and into syringe or container 30 to move stopper 31 within syringe or container 30 to expel a material, such as, for example, a medicament from autoinjector 12. One embodiment of plunger 42 is shown in FIGS. 13A-13D. In this embodiment, plunger 42 comprises an upper rod 400 at its distal end, a lower rod 500 at its proximal end and a body 420 between them. Upper rod 400 connects to the lower rod 500 at its proximal end. Upper rod 400 comprises four (4) rims 402 perpendicular to each other and forming a cross shaped cross section. Lower rod 500 connects to upper rod 400 at its distal end and to stopper 31 at its proximal end. Lower rod 500 comprises four (4) rims 502 perpendicular to each other and forming a cross shaped cross section. At its proximal end, lower rod 500 has a flat round base 506 to access stopper 31. At its distal end below body 420, lower rod 500 includes a projection 508 disposed on one of the rims for orientation purposes. In several aspects, lower rod 500 has a larger diameter than upper rod 400. In various aspects, upper rod 400 can have a length of about 25 mm and lower rod 500 can have a length of about 40 mm. In some aspects, flat round base 506 can have a diameter of about 5 mm.

Body 420 of plunger 42 comprises a lower cylindrical portion 422, an upper cylindrical portion 424 and a mid-portion 440 between them. Lower cylindrical portion 422 has a smaller diameter than that of upper cylindrical portion 424 and is configured to fit with constrainer 38. In some embodiments, lower cylindrical portion 422 can have an outside diameter of about 8 mm and upper cylindrical portion 424 can have an outside diameter of about 10 mm. At its distal end upper cylindrical portion 424 comprises a bayonet 450 having a semi rectangular U shape 452 configured to couple with housing top 20. At its distal end, upper cylindrical portion also contains a spring guide 454, and in some aspects, two spring guides, spaced apart from and facing one another and configured to facilitate that movement of plunger spring 44. In some embodiments, upper cylindrical portion 424 contains two bayonets 450 spaced apart from one another. Mid portion 440 comprises a lug 430 and, in some aspects, two lugs spaced apart from and facing one, both another configured to prevent plunger 42 from firing until autoinjector 12 is actuated. Body 420 of plunger 46 also includes an aperture 460 extending from upper cylindrical portion 424 to lower cylindrical portion 422 and configured to receive plunger spring 44. In some embodiments, plunger 42 is monolithic.

Figure 14A:
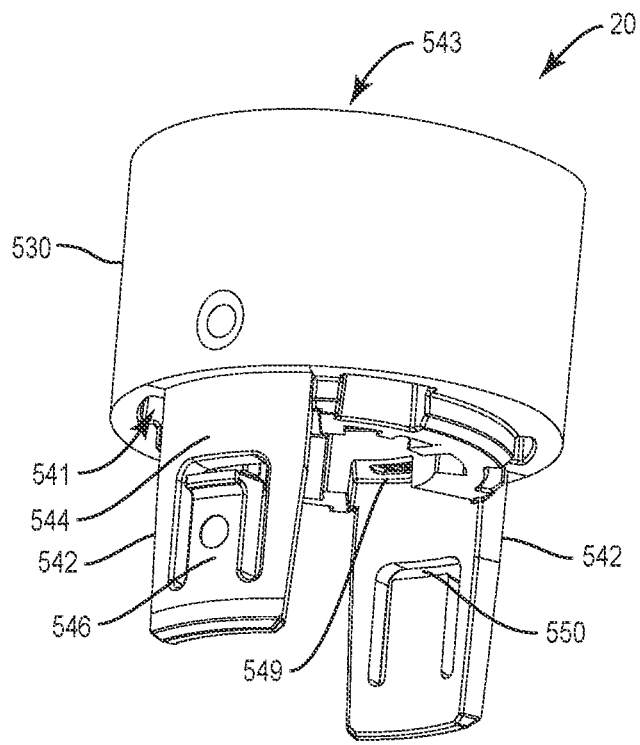
FIGS. 14A and 14B are perspective views of a housing top of the device in FIG. 2.
Figure 14B:
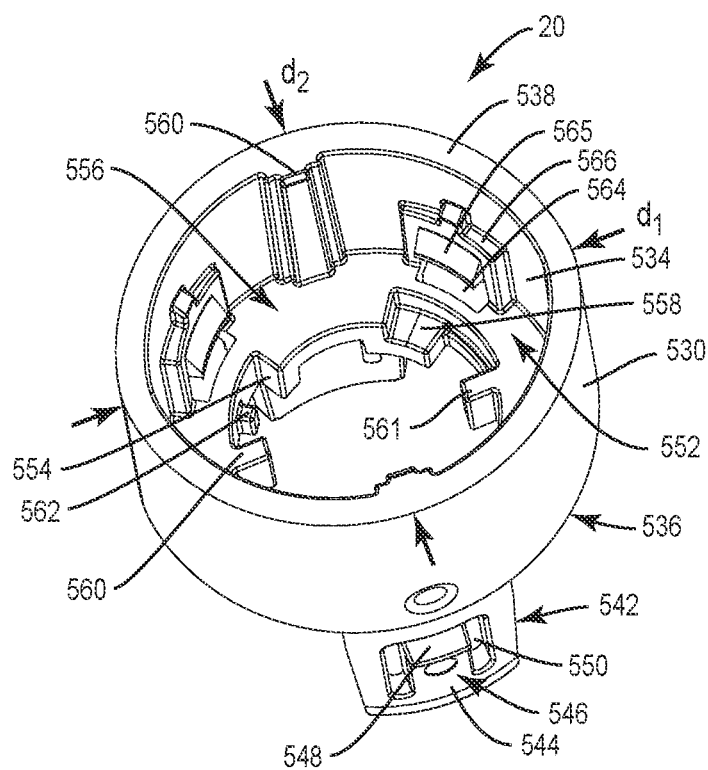

In various embodiments, housing top 20 is coupled with housing 18 at the proximal end and, at the distal end, housing top 20 is coupled to housing top insert 22. One embodiment of housing top 20 is illustrated in FIGS. 14A-14B. Housing top 20 comprises tubular, substantially oval body 530 having a proximal opening 541, a distal opening 543, a proximal edge 536, a distal edge 538 and a wing 542. In various aspects, body 530 can have an oval profile, wherein the major axis $d_1$ of the oval profile is about 28 mm and the minor axis $d_2$ is about 25 mm. In other aspects, the length of body 530 can be about 15 mm. Wing 542 is disposed at proximal edge 536 of tubular body 530, wing 542 having a retaining clip 544 configured to snap into housing 18. In some aspects, retaining clip 544 has a clip body 546 attached to the proximal edge of wing 542 and a snap portion 548 at the distal edge 549 of retaining clip 544. Surrounding retaining clip 544 is a substantially rectangular cutout 550, which together with retaining clip 544 and snap portion 548 is configured to secure housing 18. In some aspects, cutout 550 forms a U shape around a retaining clip 544. In other aspects, tubular body 530 of housing top 20 comprises two wings 542 spaced apart from and facing one another. In many aspects, wings 542 can have a length of about 15 mm.

In various aspects, at proximal edge of tubular body 530, housing top 20 comprises a mechanism 552 for locking in plunger 42. Mechanism 552 comprises a platform 554, a frame 566 around a cutout 564 and an alignment guide 560. Frame 566 abuts tab 565, which tab projects inwards tubular body 30 configured to retain securely housing top insert 22. In some aspects, mechanism 552 includes four frames 566 around four cutouts 564, having each a tab 565 and two alignment guides 560, all spaced apart from one another. Platform 554 comprises a lower step 556 disposed adjacent wing 542, a bayonet upper face 558 which couples with bayonet 450 of plunger 42, a longer tooth projection 561 and a shorter tooth projection 562, all configured to receive and secure the upper cylindrical portion 424 of plunger body 420. In other embodiments, tubular body 530 includes an alignment guide 560 disposed midway between lower step 556 and distal edge 538. In some aspects, tubular body 530 includes two alignment guides 560 spaced apart from and facing one another. In various aspects, housing top 20 is monolithic.

Figure 15A:
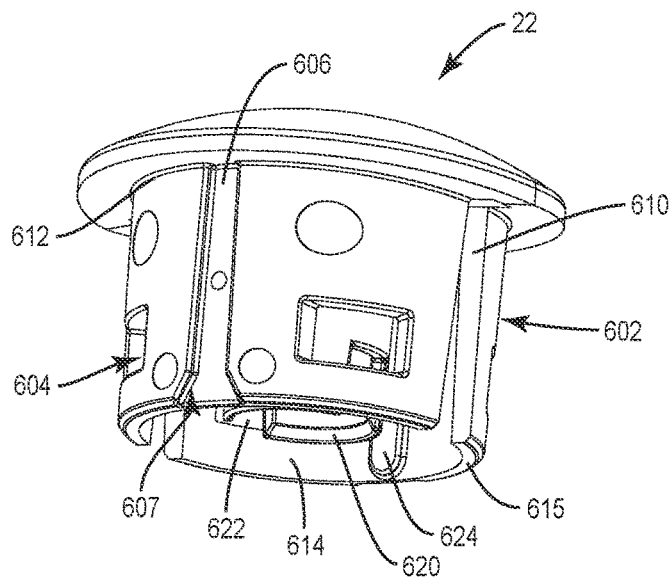
FIGS. 15A, 15B, and 15C are perspective views of a housing top insert of the device in FIG. 2.
Figure 15B:
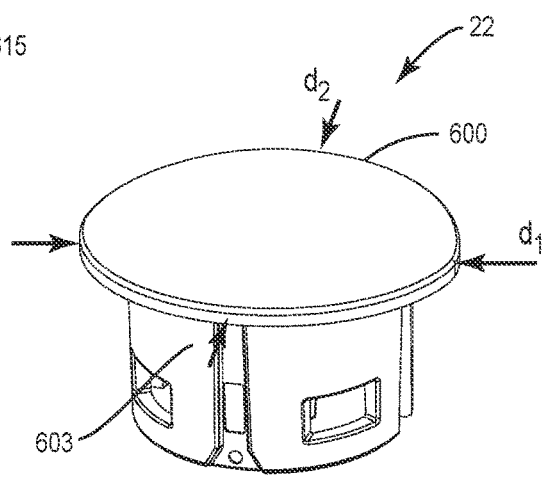
Figure 15C:
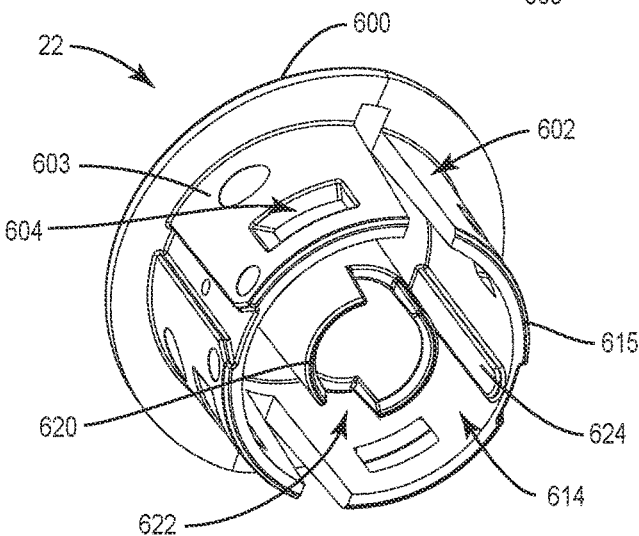

In many embodiments, housing top 20 is coupled to housing top insert 22. One embodiment of housing top insert 22 is illustrated in FIGS. 15A-15C. Housing top insert 22 comprises a convex, substantially oval top 600 and a tubular body 602 attached to oval top 600 at distal end 612. In various aspects, oval top 600 can have a substantially oval profile, wherein the major axis $d_1$ of the oval profile is about 28 mm and the minor axis $d_2$ is about 25 mm. At proximal end, tubular body 602 has proximal opening 614 configured to couple with housing top 20. In various aspects, tubular body 602 is defined by wall 603, the wall comprising cutout 604 disposed towards the proximal end of wall 603 and configured to receive tabs 565 of housing top 20. In some embodiments, the height of wall 603 is about 13 mm. Wall 603 further comprises assembly compliance V shaped slot 610 and a V shaped orientation feature 606 having two ramps 607 at proximal edge 615 of tubular body 602. In various embodiments, wall 603 comprises, four cutouts 604, two slots 610 and two orientation features 606. Internally, tubular body 602 includes an alignment guide 624. Housing top insert 22 further includes a plunger spring well 620, cylindrically shaped and having U shaped cutouts 622, spaced apart from one another. At its distal end 626 (not shown), spring well 620 is centrally disposed and attached to convex top 600. In various aspects, spring well 620 can have an outside diameter of about 7 mm. Spring well 620 is configured to receive upper rod 400 of plunger 42 and plunger spring 44. In various embodiments, housing top insert 22 is monolithic.

A plunger spring 44 is illustrated in one embodiment in FIG. 16B. Plunger spring 44 is disposed in housing top insert 22. When autoinjector 12 is in use, plunger spring 44 engages plunger 42 to push syringe stopper 31 to expel a material, for example a medicament from syringe or container 30 of autoinjector 12. In some embodiments, when extended, the length of plunger spring 44 can be about 58 mm and an outside diameter of about 4 mm.

Skin Sensor Lock

Internally, removable cap 14 has cams 104 that drive skin sensor insert (SSI) 34 around inside the skin sensor 32 when cap 14 is assembled to autoinjector 12. As the SSI rotates, its internal lugs or pins 200 engage under an angled lock face in a modified U-slot or inverted J-slot on the surface of carriage 40. The SSI has external lugs or external retaining pins 202 that are engaged on clip slots 160 in skin sensor 32. Thus, if the autoinjector is dropped or shocked when configured for storage, skin sensor 32 is prevented from moving under inertial forces by the load path skin sensor clip slot 160—SSI external pin 196—SSI internal lug 200—carriage 40—constrainer 38—housing 18. When cap 14 is removed, cams 104 release SSI 34 from its locked position. The SSI 34 is returned to its unlocked position by the action of the skin sensor or drive spring 36 and the angled face on the modified U-slot or inverted J-slot on carriage 40.

Activating the Injector Over Injection Site

As autoinjector 12 is pressed onto the injection site, skin sensor 32 retracts into it, initiating the operating sequence and allowing needle 28 to emerge. The movement of autoinjector 12 relative to skin sensor 32 is subject to a threshold that requires the user to apply an initially high force of 23 N to start the operation, after which, the force can drop to 9 N. The threshold force is generated by the interaction of cam face 171 on the skin sensor driving the collar 16. The movement of the collar 16 is resisted by a reverse-angled pair of faces between the collar 16 and carriage 40 that are held in contact by the skin sensor or drive spring 36. In some embodiments, the reverse-angled faces are face 64 of collar 16 and face 233 of carriage 40.

Once the threshold is overcome, the autoinjector internal mechanism controls the start of injection relative to the depth of needle insertion. As autoinjector 12 is pressed down against the injection site, skin sensor 32 compresses skin sensor spring 36. This skin sensor spring acts on collar 16 that imparts a torque onto carriage 40 component via a helical cam 228 on carriage 40, whose rotation is controlled by features on the inside of skin sensor 32, for example, skin sensor insert 34.

When skin sensor 32 is pressed sufficiently to achieve the target needle insertion depth, it releases carriage 40 to rotate, which rotates plunger 42. Plunger 42 is held back against the force of the injection spring or plunger spring 44 by bayonet feature 558 in the housing top 20, and when it is rotated, it becomes free to move under the plunger spring or injection spring 44 force and thus plunger 42 drives stopper 31 in syringe or container 30, expelling the dose. Syringe or container 30 is suspended in the center of carriage 40 by constrainer 38 which transmits the needle insertion and injection loads into housing 18. Constrainer 38 has two feedback arms 300 that are flicked by the plunger 42 as it passes, thus creating audible/tactile feedback to indicate that the dose has been delivered.

Withdrawal of Injector from the Injection Site

Once the injection is complete and time allowed for diffusion of the dose, the user withdraws autoinjector 12 from the injection site. As autoinjector 12 is withdrawn, needle 28 is pulled out and skin sensor 32 advances to cover it. As needle 28 comes free, skin sensor 32 is then locked in an advanced position (compared to its starting position) by further rotation of carriage 40 under the torque generated by the skin sensor spring-collar-helical cam system, thus preventing any contact with the contaminated sharp. This advanced position also prevents cap 14 from being securely replaced. In this state, stopper 31 and the red plunger 42 are visible in the autoinjector window, a further indication to the user that the autoinjector has been successfully used.

A cap and rigid needle shield removal operation is shown in one embodiment in FIGS. 18A to 18C. FIG. 18A illustrates syringe or container 30 encased in a flexible needle shield 26 surrounded by rigid needle shield 24. FIG. 18A also illustrates cap assembly 13 comprising removable cap 14 and cap insert 15. Clips 128 of cap insert 15 engage with rigid needle shield 24 when autoinjector 12 is assembled as shown in FIG. 18b. On removal of cap 14, clips 128 of cap insert 15 catch on the end of flanges 27 of the rigid needle shield 24 to remove it as shown in FIG. 18c.

Figure 19A:
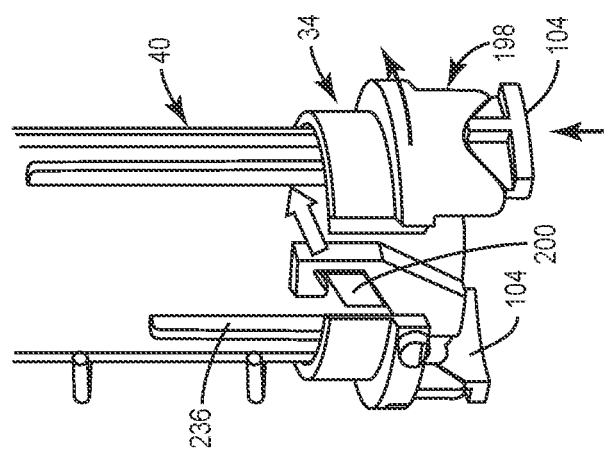
FIGS. 19A, 19B, 19C and 19D are perspective views of components of an embodiment of the device in FIG. 3.
Figure 19B:
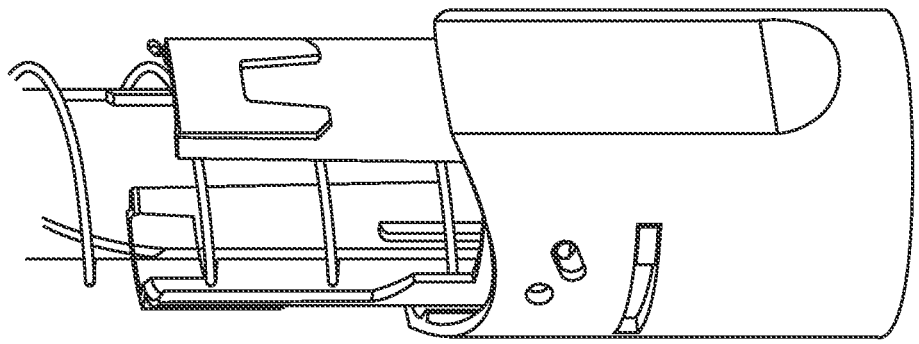
Figure 19C:
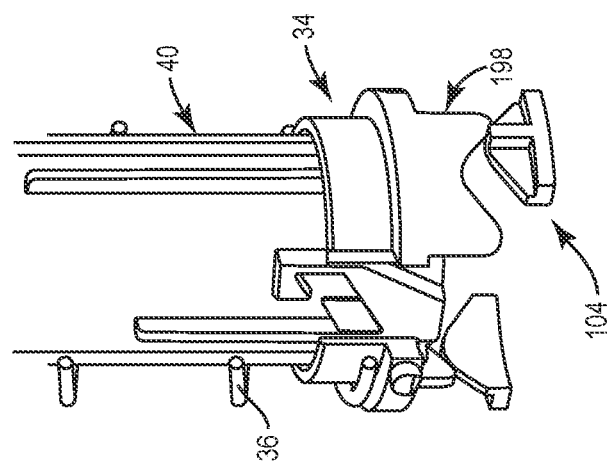
Figure 19D:
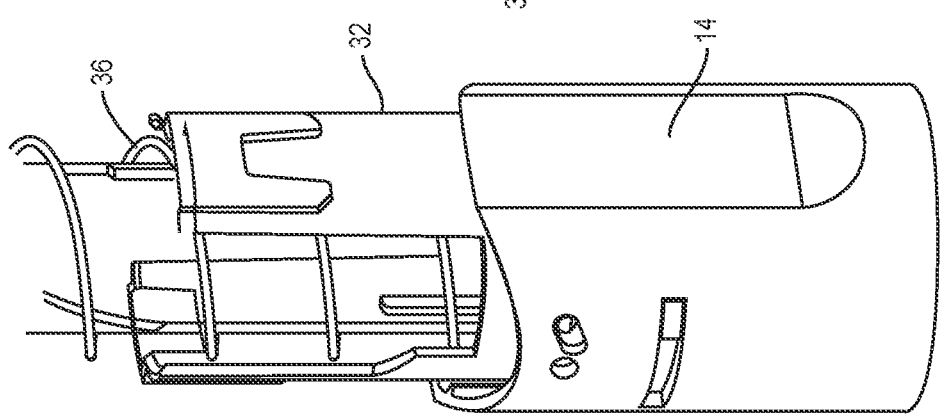

A skin sensor lock operation is shown in one embodiment in FIGS. 19A-19D. FIG. 19A illustrates the start of assembly of skin sensor 32 and cap 14. On assembly of cap 14, cams 104 of cap 14 engage with the cams 198 of skin sensor insert 34 and cause them to turn. FIG. 19B is a cut away view showing cap cams 104 in first contact with skin sensor insert cams 198. FIG. 19C illustrates a fully assembled cap and skin sensor including its skin sensor insert. FIG. 19D is a cutaway view showing cap cams 104 fully engaged with skin sensor insert cams 198. In the embodiment shown in FIG. 19D, skin sensor insert 34 has turned so that its inner lugs or pips 200 are now engaged with lock features of carriage 40. On removal of cap 14, skin sensor spring 36 drives skin sensor insert 34 down the slope of inverted J rib or rail 236 of carriage 40 and out of engagement with the carriage lock feature. A skin sensor spring 36 is illustrated in one embodiment in FIG. 16A. In some aspects, when extended, skin sensor spring 36 can have a length of about 75 mm and an outside diameter of about 17 mm.

Figure 20E:
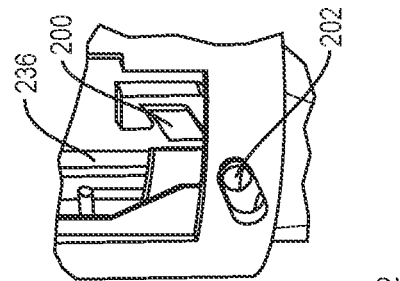
FIGS. 20A, 20B, 20C, 20D and 20E are perspective views of components of an embodiment of the device in FIG. 3.
Figure 20D:
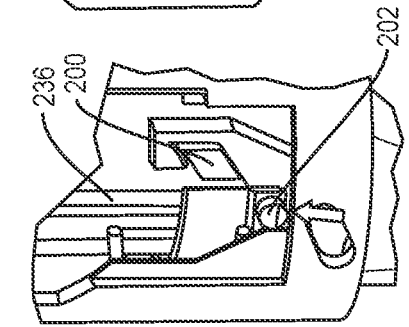
Figure 20C:
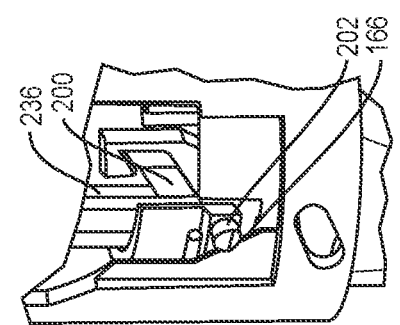
Figure 20B:
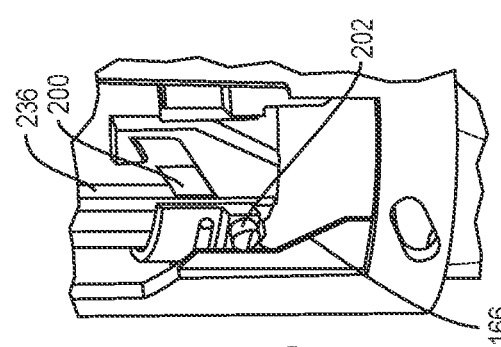
Figure 20A:
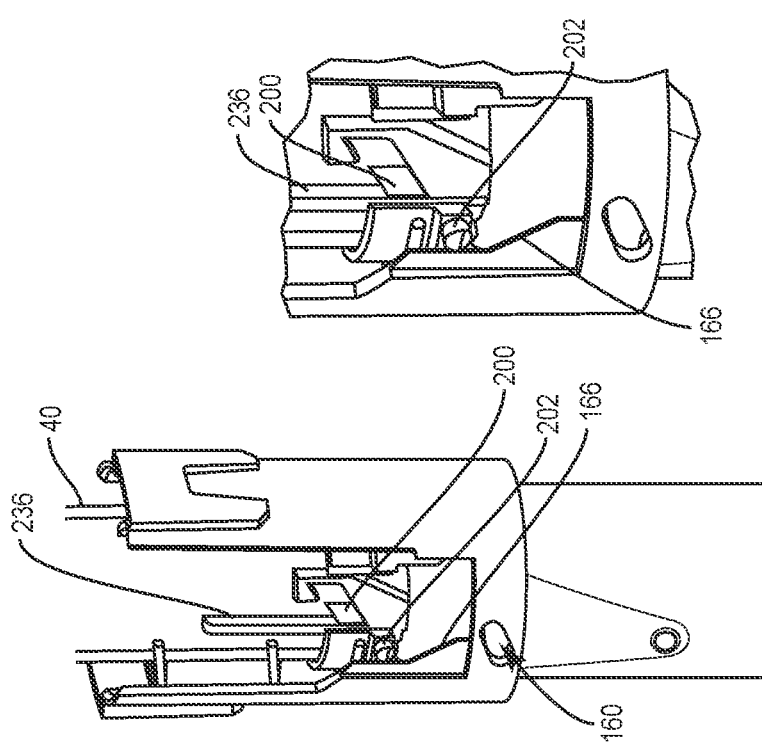

FIGS. 20A-20E illustrate an embodiment of the skin sensor assembly operation. Before the assembly operation begins, skin sensor insert external retaining pin 202 needs to be engaged into the angled skin sensor clip slot 160 in the skin sensor 32. As a result, skin sensor insert 34 would be restrained before this operation starts. In FIG. 20A, skin sensor insert 34 is shown before skin sensor insert pin 200 has moved into the inverted J rib of the carriage 40. In FIGS. 20B and 20C as the skin sensor is pushed on, the skin sensor insert pin 200 rubs along the cam face 166 in the skin sensor so that the skin sensor insert rotates and engages inner lug 200 into the carriage lock feature. In FIGS. 20D and 20E, the skin sensor insert pin 200 moves into the U-shaped angled channel or slot 237 of the inverted J rail. This is accomplished by continuing to press the skin sensor 32 onto the subassembly, the skin sensor insert pin 200 is driven into the U-shaped slot 237.

Figure 21C:
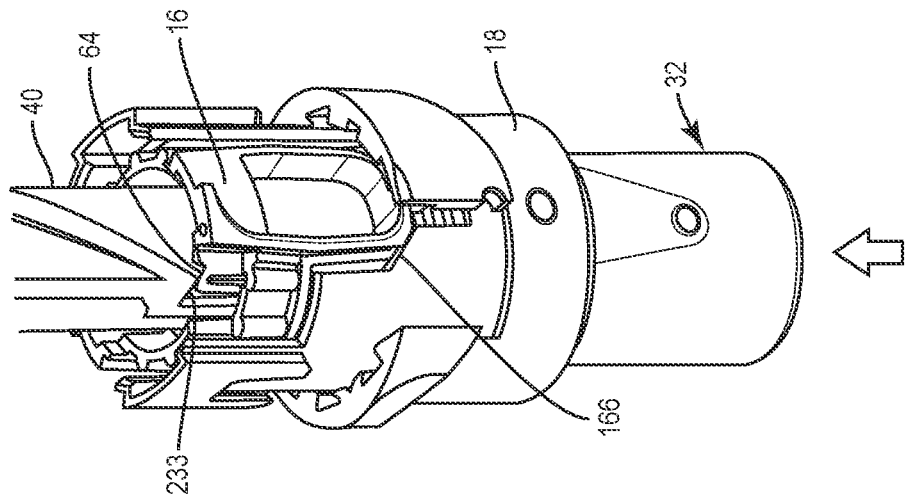
FIGS. 21A, 21B, 21C, 21D and 21E are perspective views of components of an embodiment of the device in FIG. 3.
Figure 21B:
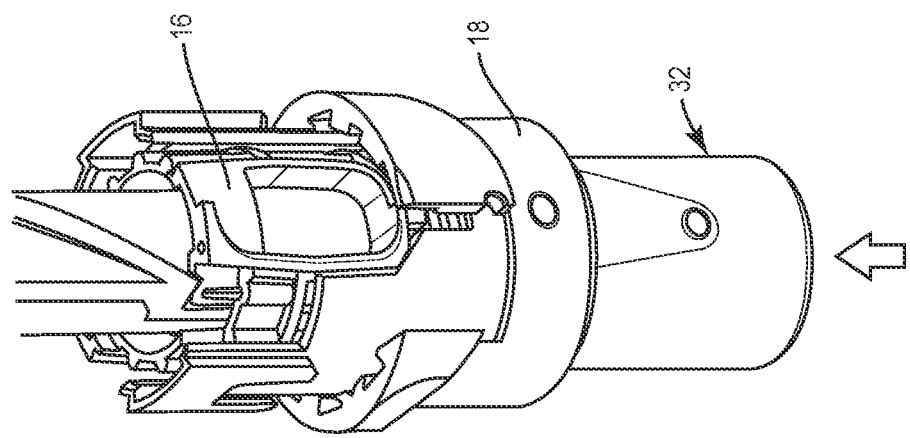
Figure 21A:
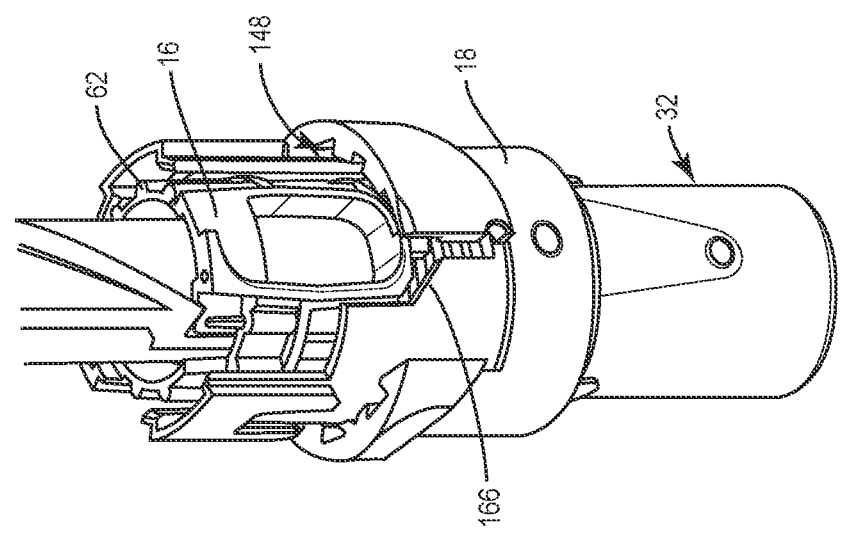
Figure 21E:
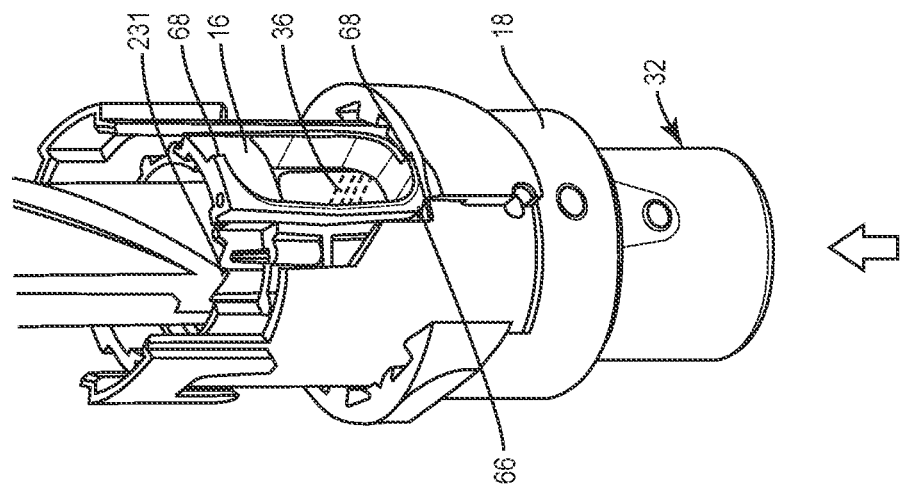
Figure 21D:
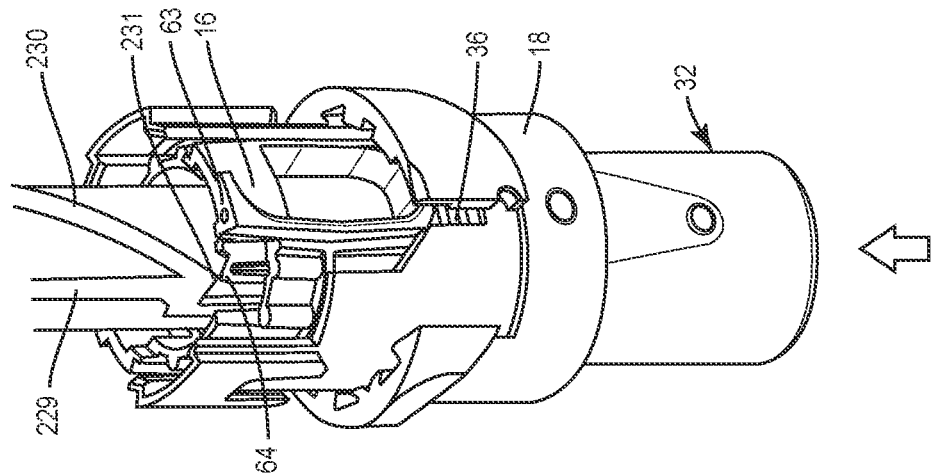

FIGS. 21A-21E illustrate an embodiment of actuation threshold showing the interaction among skin sensor 32, collar 16 and carriage 40. FIG. 21A shows the skin sensor 32, collar slot 148 in housing 18 and carriage 40 in a ready-to-use state. FIG. 21B illustrates the initial movement of skin sensor 32. FIG. 21C illustrates a further movement of skin sensor 32, wherein the skin sensor cam 166 drives collar 16 to rotate causing the collar threshold face 64 to slide past carriage threshold face 233 generating a threshold reaction force. In the embodiment of FIG. 21D, at the point of release from threshold faces between collar threshold face 64 and carriage point 231, collar 16 has rotated so that threshold faces are at the point 231 of the carriage and point 63 of the collar of slipping past each other. In the embodiment of FIG. 21E, after threshold, in the needle insertion phase, collar 16 has moved onto carriage 40 main helical cam 228. A force from skin sensor or drive spring 36 on collar 16 generates a torque on carriage 40. In this embodiment, skin sensor 32 has moved off collar drive cam 66 and collar 16 is now against its running face 68 in the housing 18.

Figure 22:
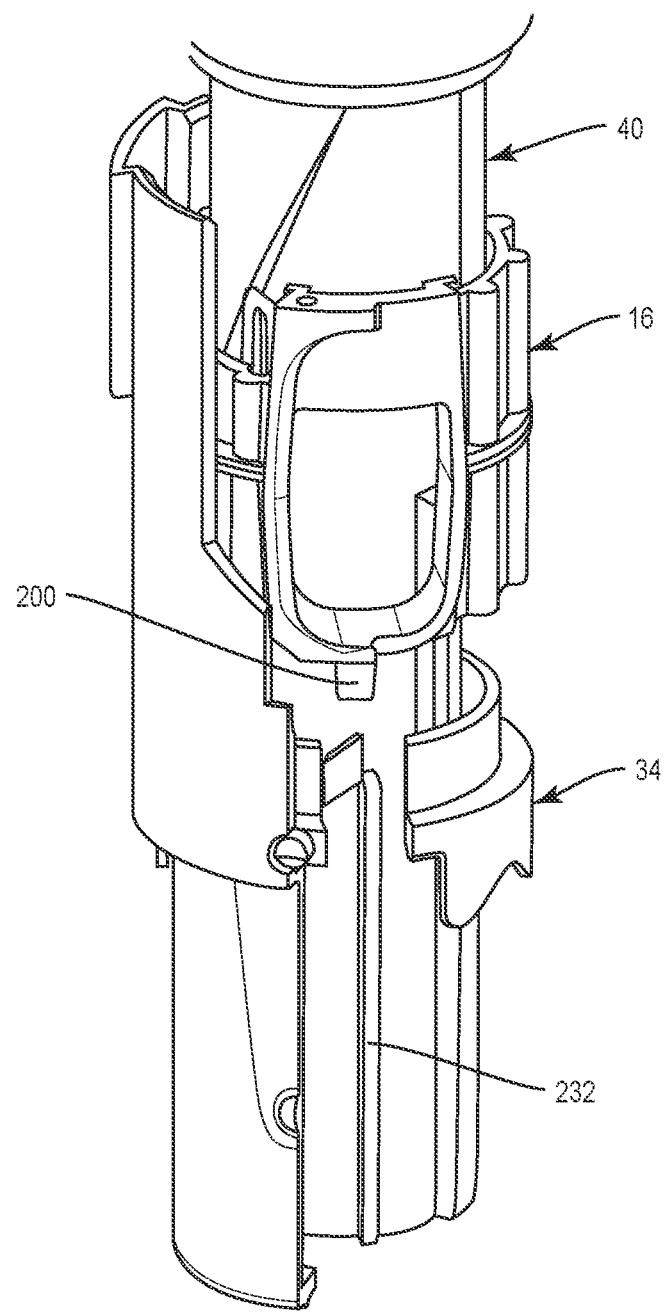
FIG. 22 is a perspective view of components of an embodiment of the device in FIG. 3.

In the embodiment of FIG. 22, in order to rotate carriage 40 skin sensor spring 36 (not shown) applies a load on the helix form 228 of carriage 40 through collar 16. The rotation of carriage 40 can be arrested by abort rib or rail 232 which comes into contact with skin sensor insert pin 200. In this embodiment, skin sensor insert pin 200 is shown at the limit of insertion prior to the transition to the injection phase. In this phase, if a user aborts the insertion of the autoinjector, and withdraws needle 28 prior to the transition to the injection phase, skin sensor 32 will advance but will not lock. On a subsequent attempt, the autoinjector will operate, but without the threshold force required to actuate it.

In the embodiment illustrated in FIGS. 23A and 23B, autoinjector 12 is illustrated at the point of transition to the start of injection phase. In FIG. 23A, the force of drive or skin sensor spring 36 (not shown) exerts a torque on carriage 40. Skin sensor insert lug 200 is going over the top of abort rib 232 onto injection rib or rail 234 thereby allowing carriage 40 to turn. In FIG. 23B, carriage cars or arms 226 start to rotate plunger 42. Plunger 42 is retained in the housing top 20 through its bayonet feature 450.

Figure 24B:
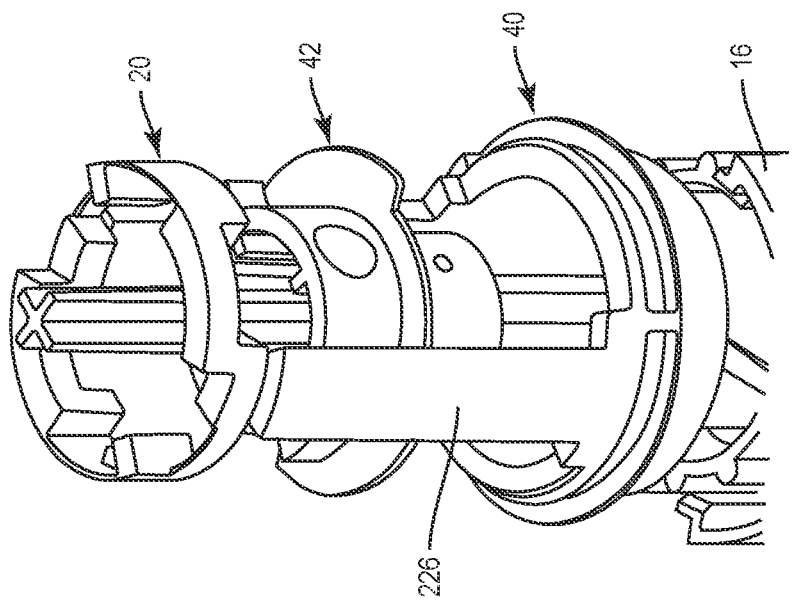
FIGS. 24A and 24B are perspective views of components of an embodiment of the device in FIG. 3.
Figure 24A:
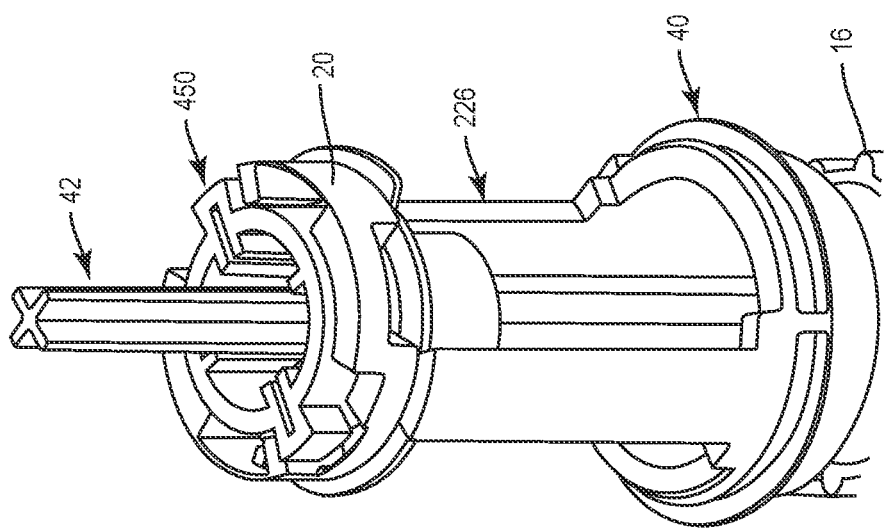

In the embodiment shown in FIGS. 24A and 24B, the rotation of the carriage 40 has pushed plunger 42 off the shelf of its bayonet 450 and plunger driver 42 is free to advance stopper 31 under the force of plunger spring 44 (not shown).

Figures 25A, 25B, 25C, 25D:
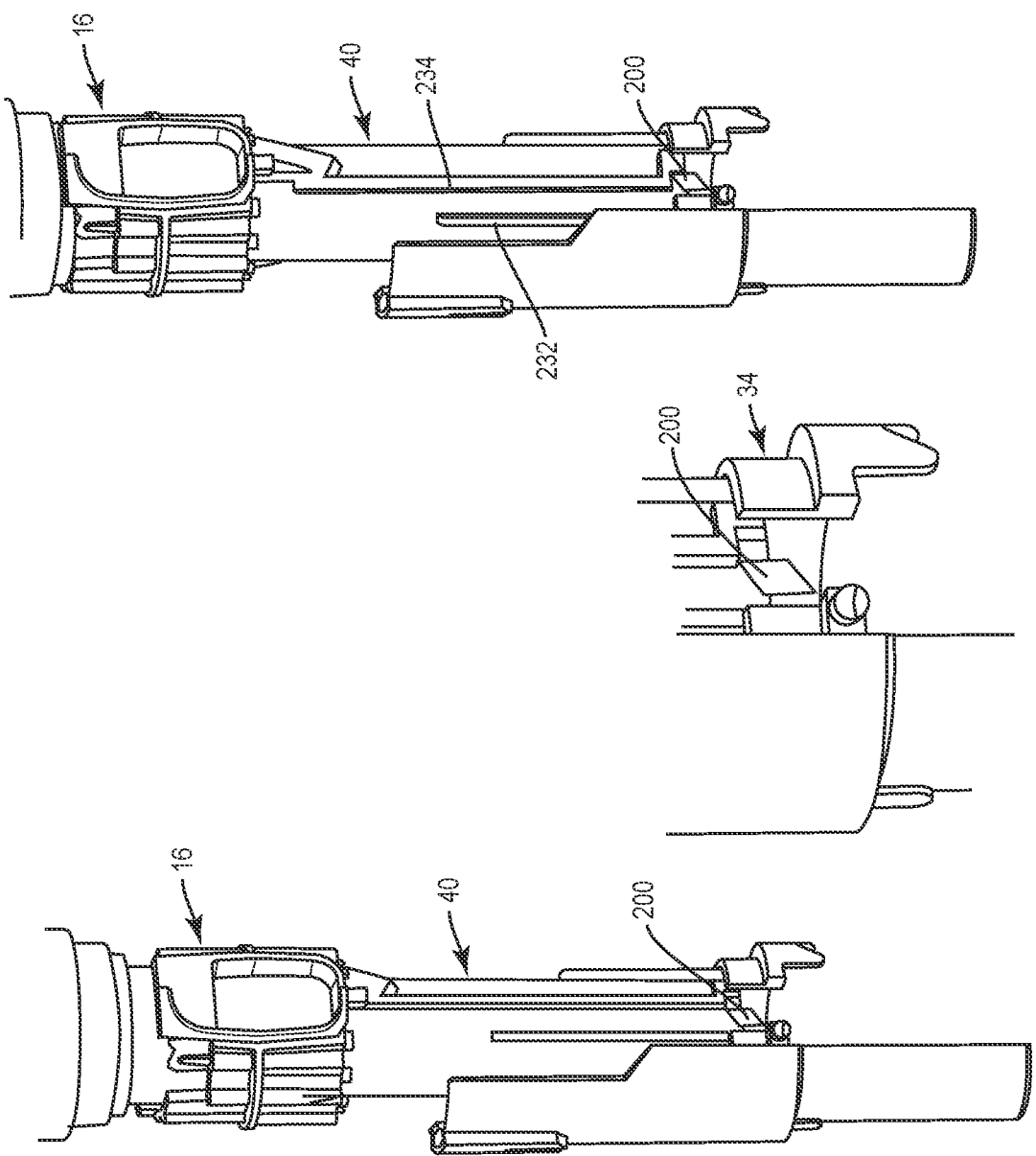
FIGS. 25A, 25B, 25C and 25D are perspective views of components of an embodiment of the device in FIG. 3.
Figure 26:
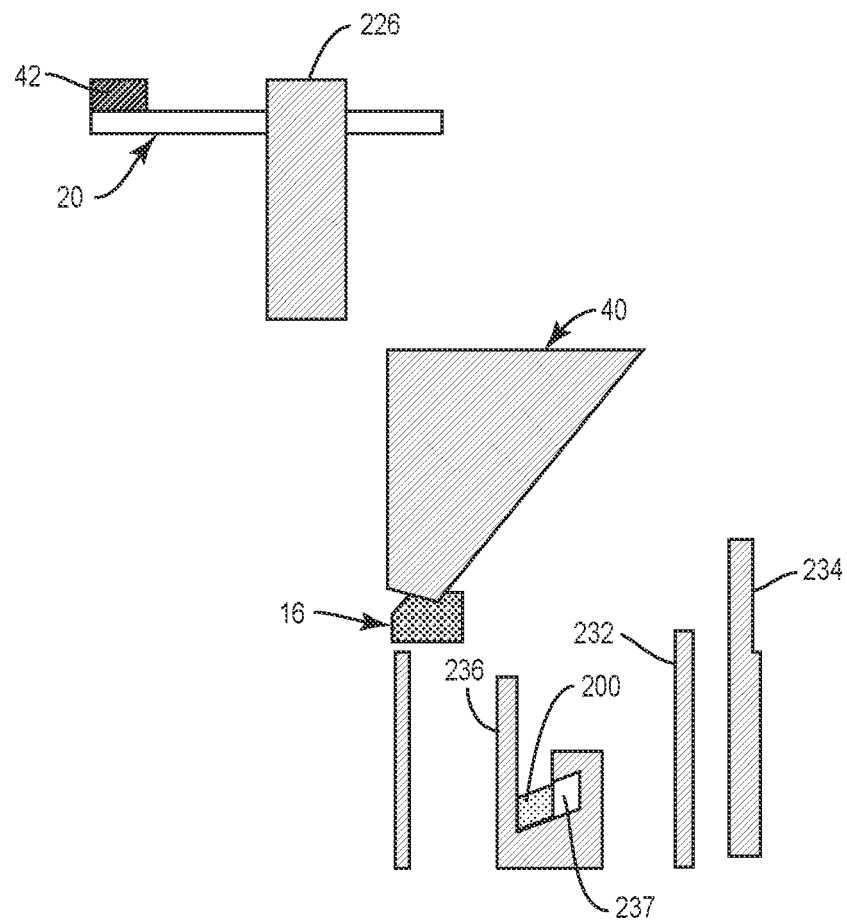
FIGS. 26, 27, 28, 29, 30, 31, 32, 33, 34, 35, and 36 are schematic diagrams of components of an embodiment of the autoinjector in FIG. 3.

The embodiment illustrated in FIGS. 25A to 25D shows the interaction among the collar, carriage and skin sensor insert in the lock-out phase after the needle is withdrawn. In FIG. 25A, collar 16 is still applying a torque to carriage 40. In FIG. 25B, carriage 40 is reduced or prevented by skin sensor insert lug 200 from turning against the carriage injection rib or rail 234. FIGS. 25C and 25D illustrate that when needle 28 (not shown) is withdrawn sufficiently to that the skin sensor insert lug 200 falls off the end of injection rib 234 and into the lock-out feature.

The operation of the delivery device 10, in some aspect, autoinjector 12 is also shown schematically on FIGS. 26-36. In the embodiment shown in FIG. 26, autoinjector 12 is at rest. Prior to the engagement between the cap cam 104 and the W shaped cam 198 of skin sensor insert 34, parallelogram lug 200 of skin sensor insert 34 sits at the bottom of the U-slot 237 in the inverted J rib 236 of carriage 40 under the downwards load from the skin sensor spring 36 (not shown). The upper end of the skin sensor spring 36 acts on collar 16, keeping the threshold features in engagement. Skin sensor spring 36 (not shown) acts upwards on collar 16 and downwards on skin sensor insert 34.

Figure 27:
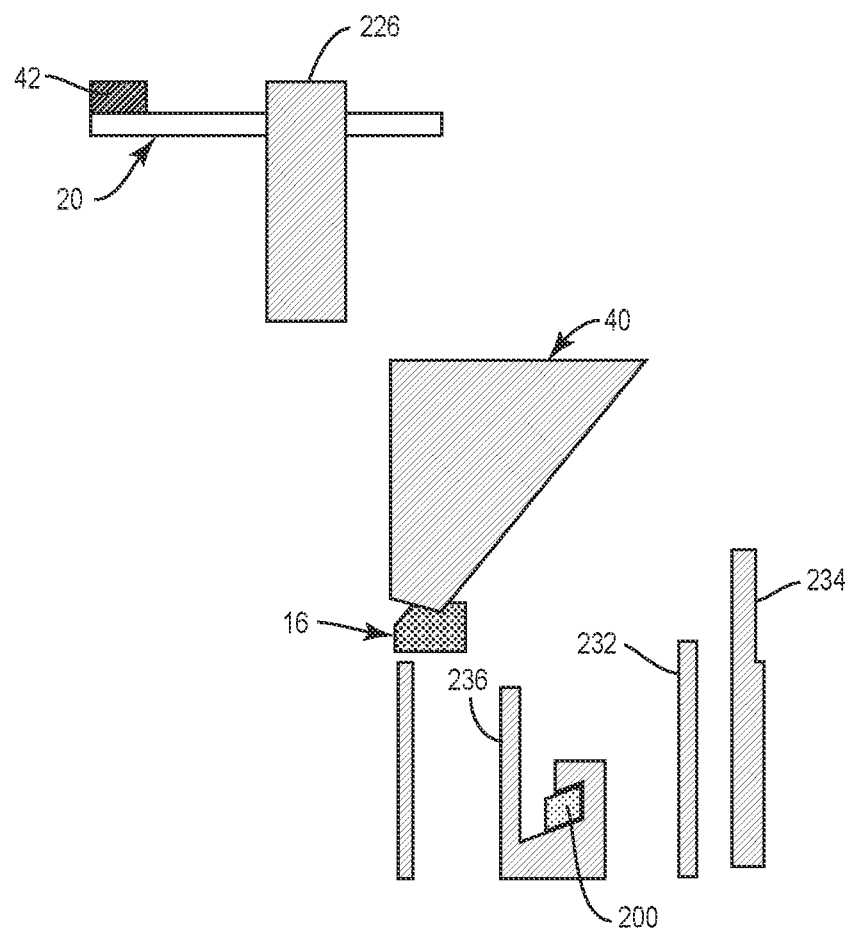

In the embodiment of FIG. 27, autoinjector 12 is still at rest in the storage state. Lugs 200 of skin sensor insert 34 are pushed to the right by the action of the cap cam 104, thus engaging the skin sensor insert lugs 200 into the locking features of the carriage 40. Carriage 40 cannot rotate because collar 16 is engaged at the bottom of the carriage cam 228 (not shown). Skin sensor spring 36 (not shown) acts upwards on collar 16 and downwards on skin sensor insert 34. Plunger 42 carries the load from the injection or plunger spring 44 (downwards in this diagram, not shown) and is held back by housing top 20.

Figure 28:
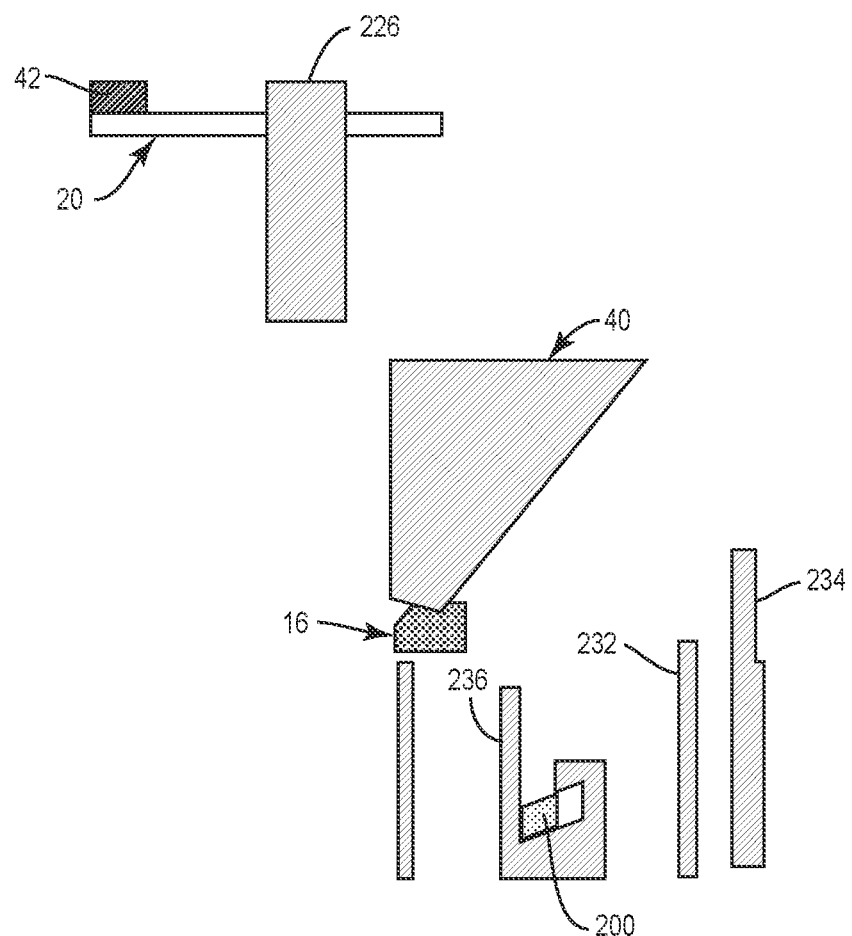

In FIG. 28, removing the cap releases the skin sensor insert 34, which is pushed out of the carriage 40 lock feature by the skin sensor spring 36 and the angled slope of the lock feature of carriage 40 (same state as prior to final assembly).

Figure 29:
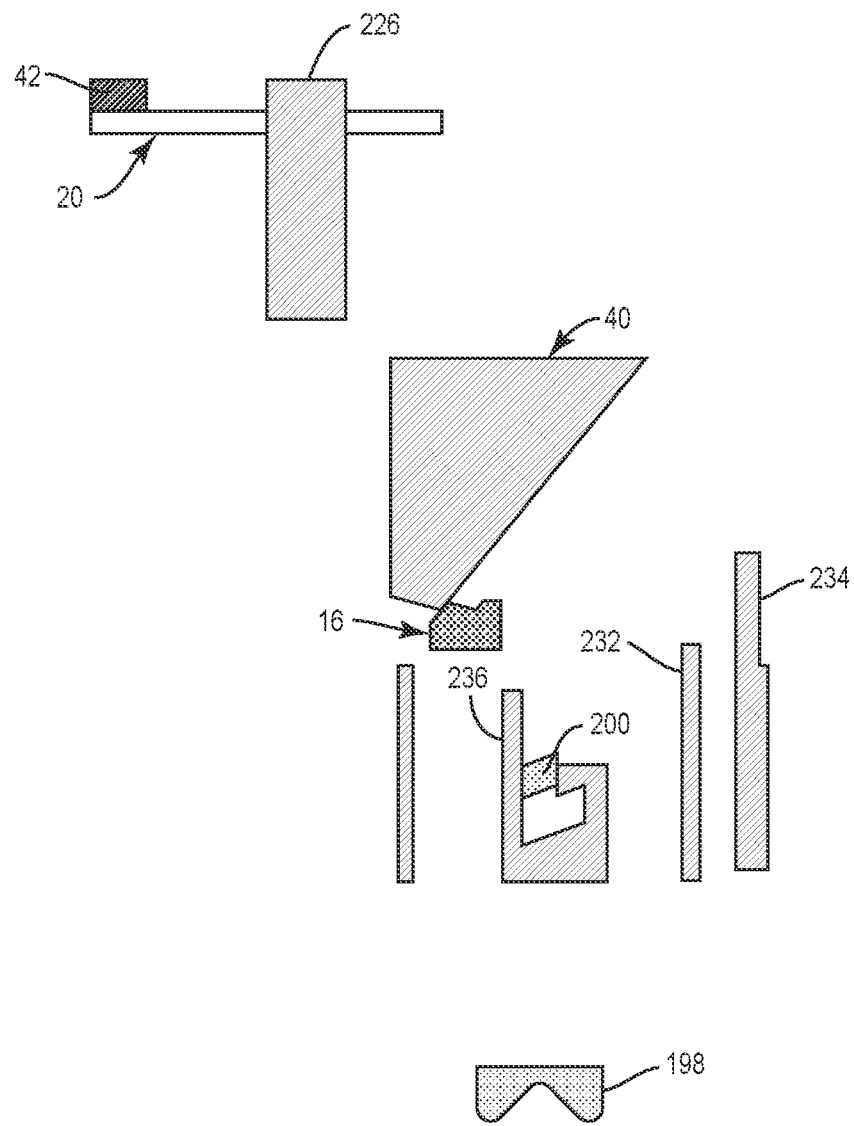

The embodiment of FIG. 29 illustrates the first movement of skin sensor 32. A threshold force mechanism is overcome. Lug 200 of skin sensor insert 34 is leaving U-shaped slot 237 of carriage 40. Collar 18 can now impart a torque on carriage 40 but the carriage has not moved yet.

Figure 30:
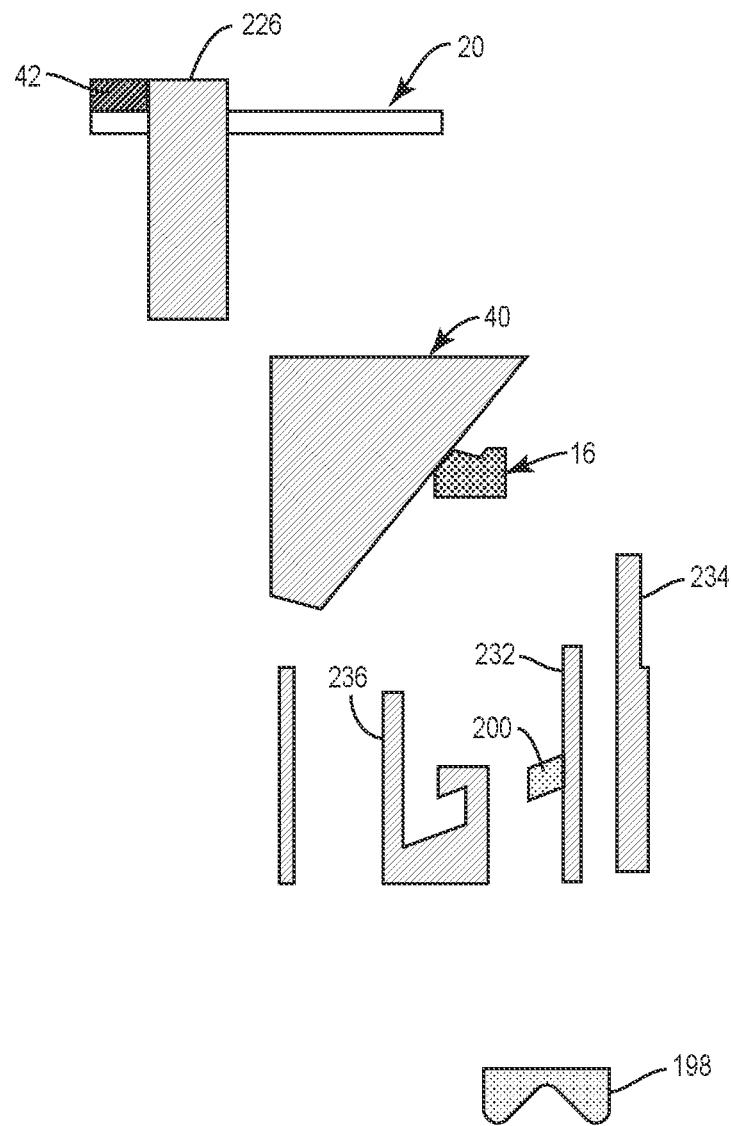

FIG. 30 illustrates the insertion of needle phase. In this phase, collar 16 has moved up under skin sensor spring 36 load and has rotationally driven carriage 40. Carriage 40 stops rotating when abort rail 232 comes into contact with skin sensor insert lug 200. Carriage top car or arm 226 has rotated up to plunger lug 430 (not shown). Further needle insertion compresses skin sensor spring 36.

Figure 31:
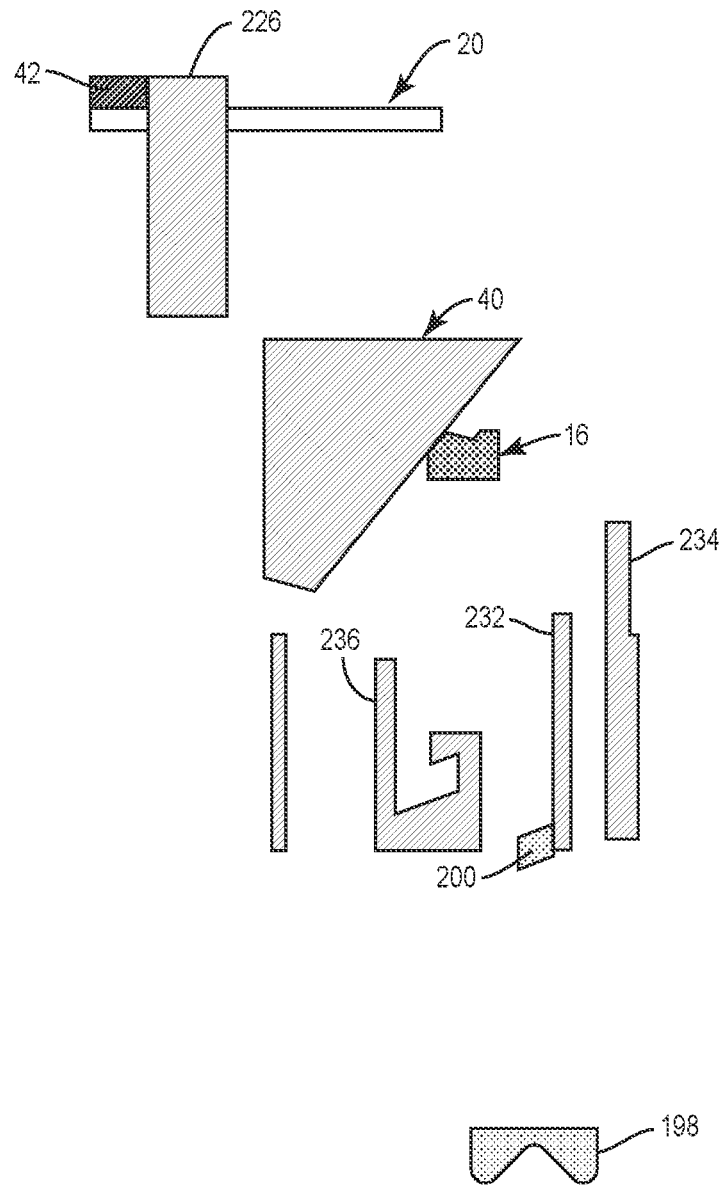

The embodiment of FIG. 31 illustrates an aborted insertion which occurs when a user withdraws autoinjector 12 before fully inserting needle 28. In this embodiment, carriage 40 is unable to rotate. Skin sensor 32 covers needle 28 at same rate as the withdrawal of autoinjector 12. Skin sensor is not locked out, allowing a second attempt at insertion. In some aspects, this state may or may not occur, and is not part of the normal use sequence. Skin sensor 32 can protrude further from the body of autoinjector 12 than in the starting position.

Figure 32:
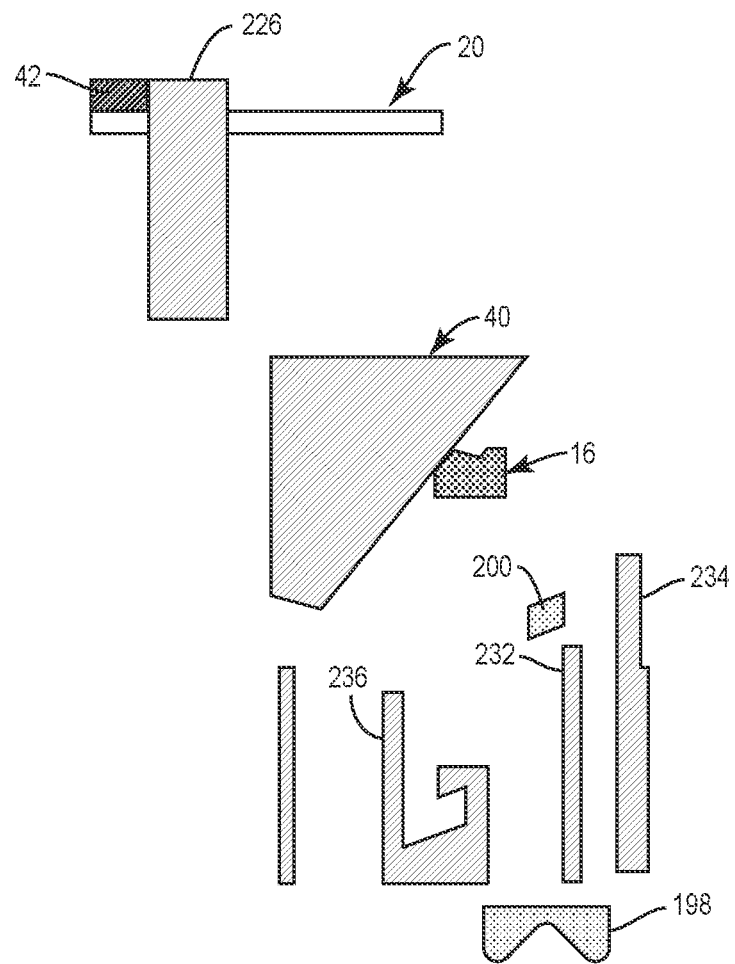

The embodiment of FIG. 32 illustrates the transition of autoinjector 12 to an injection phase. Skin sensor insert lug 200 is high enough to clear abort rail 232 and about to allow carriage 40 to rotate. At the last point before the carriage is freed to rotate, the maximum in-device spring compression is reached and autoinjector 12 is in an instantaneous state.

Figure 33:
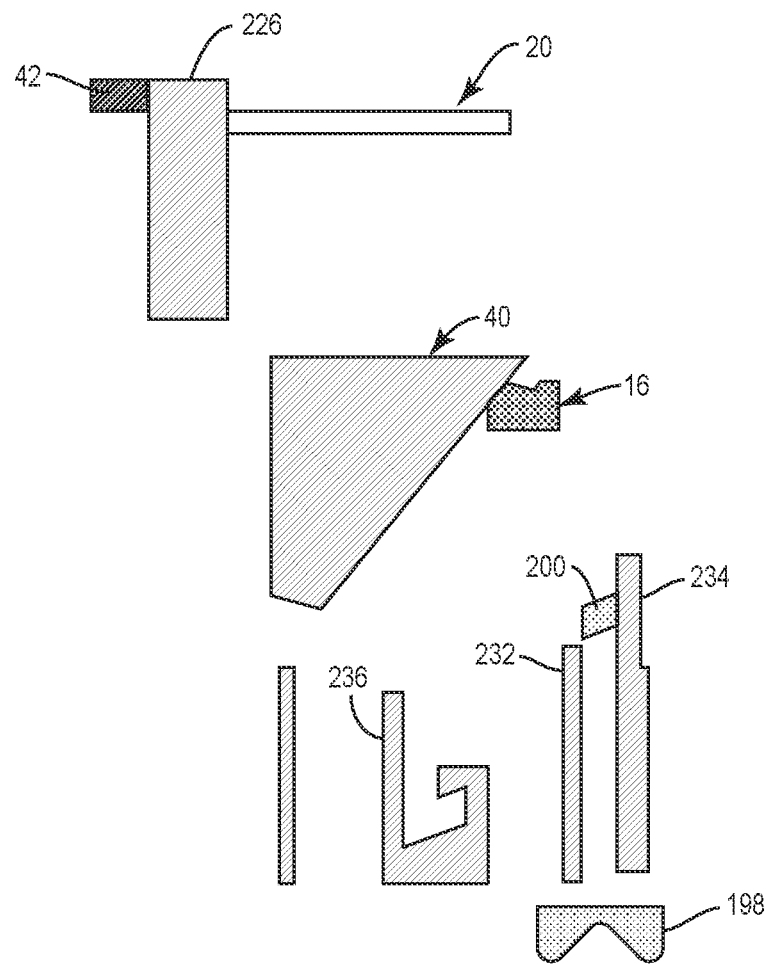

FIG. 33 illustrates the operation of autoinjector 12 in the injection phase. To start injection, plunger 42 is released. Needle 28 is fully inserted, and the skin sensor insert lug 200 has cleared abort rail or rib 232. Collar 16 is free to drive carriage 40 to rotate again and drives it until the full insertion or injection rib 234 contacts the skin sensor insert lug 200. This rotation of the carriage also frees the plunger 42 from the housing top 20 to inject (plunger 42 is shown in instantaneous state about to start its travel).

Figure 34:
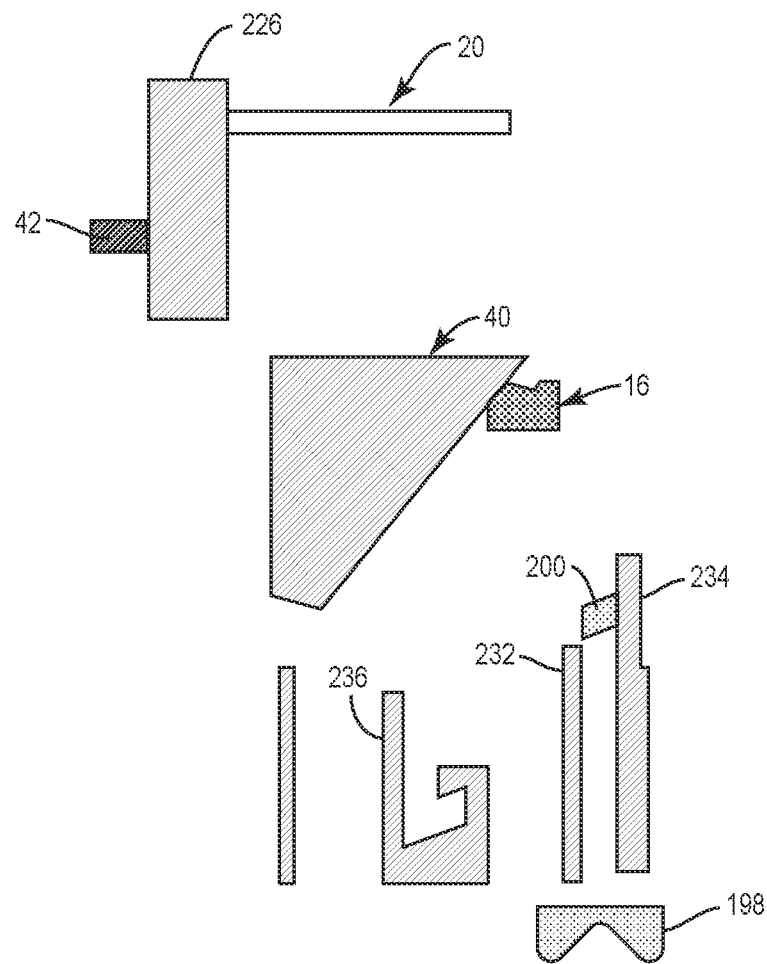

The embodiment illustrated in FIG. 34 shows a completed injection phase. In this phase, stopper 31 reaches its end stop. The injection or plunger spring 44 drives plunger 42 and hence the plunger, injecting the dose. In some embodiments, if autoinjector 12 is configured for full evacuation, then the injection end stop occurs where the stopper 31 bottoms out in the syringe or container 30. In other embodiments, if autoinjector 12 is configured for partial evacuation, then the injection end stop occurs when the plunger 42 stops on the constrainer.

Figure 35:
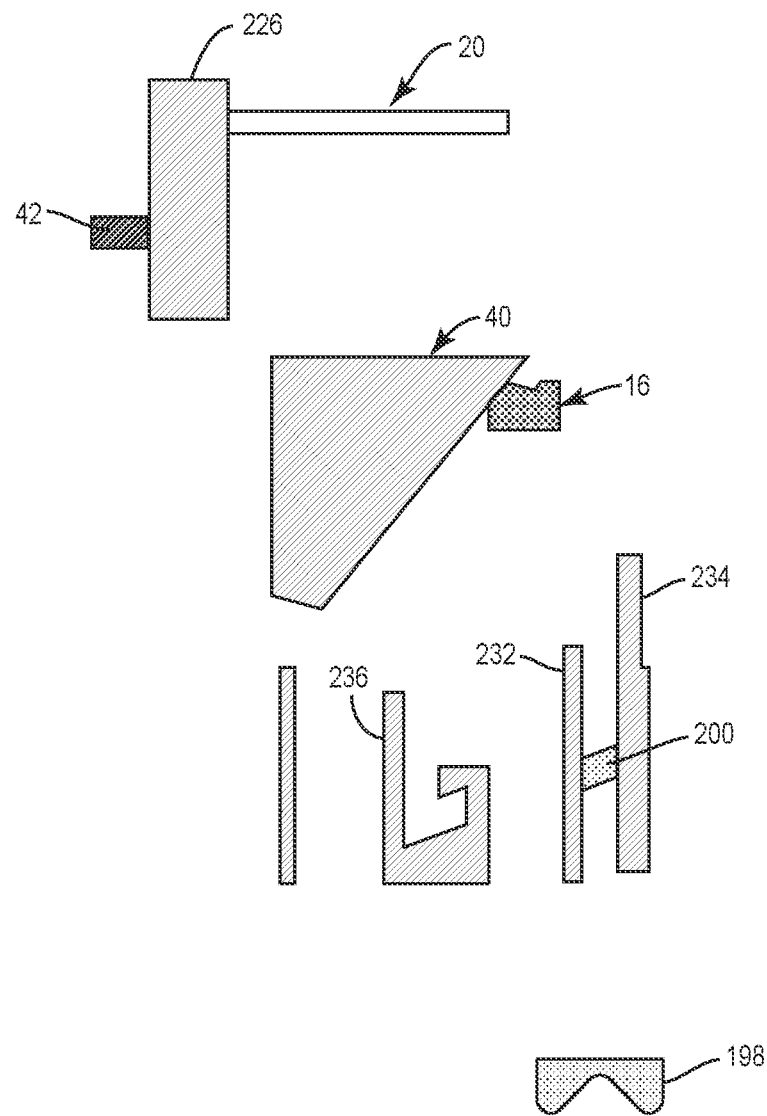

In the embodiment of FIG. 35, skin sensor 32 is extended. As the user withdraws the needle from their leg, for example, skin sensor spring 36 pushes skin sensor 32 out. Collar 18 cannot move because carriage 40 is unable to rotate as it is reduced or prevented from rotation by skin sensor insert lug 200 moving against insertion or injection rib 234.

Figure 36:
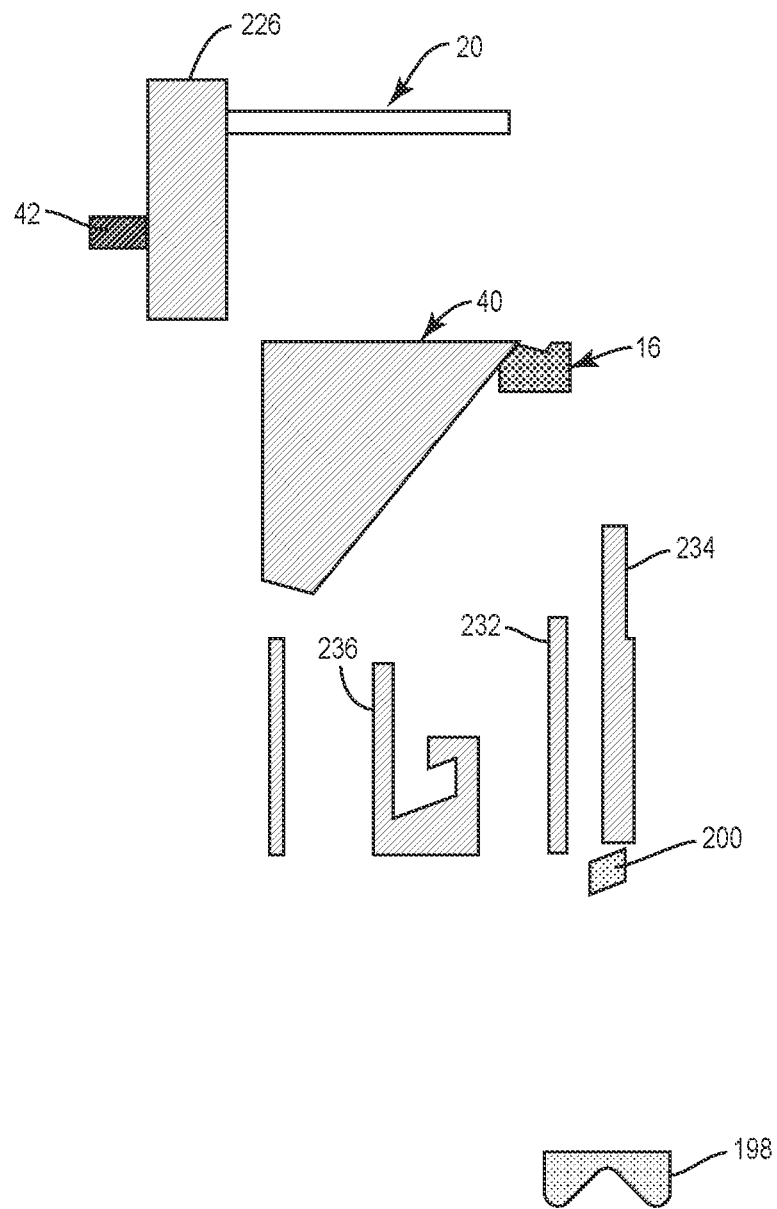

FIG. 36 illustrates skin sensor 32 locked out. Skin sensor insert lug 200 clears the full insertion or injection rail 234, allowing carriage 40 a final rotation. Collar 18 drives carriage 40 through its final rotation. Autoinjector 12 is now locked such that pushing on skin sensor 32 will not move it.

The embodiment of FIGS. 37A-37E illustrate the entire cycle of the injection phase using the delivery device 10 described in this application. In some embodiments, the delivery device 10 can be autoinjector 12. FIG. 37A illustrates autoinjector 12 in an initial storage state. FIG. 37B, shows autoinjector 12 with its cap removed and positioned against an injection site 700, for example, a skin surface. FIG. 37C shows autoinjector 12 when the safety system is activated, the needle is inserted into the injection site 700 and the plunger 42 (not shown) is released. In FIG. 37D, plunger 42 travels down to connect with stopper 31 and deliver the medicament dose from the container or syringe 30 through needle 28. FIG. 37E illustrates the autoinjector after skin sensor 32 returns to its start position to shield needle 28.

The device components (e.g., needle, cap, medicament, etc.) can be sterilized. In various embodiments, one or more components of the device to inject the medicament can be sterilized by radiation in a terminal sterilization step in the final packaging. Terminal sterilization of a product provides greater assurance of sterility than from processes such as an aseptic process, which require individual product components to be sterilized separately and the final package assembled in a sterile environment. In some embodiments, one or more components of the device can be aseptically assembled.

In various embodiments, gamma radiation can be used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproducing cells of microorganisms. Beams produced for e-beam sterilization are concentrated, highly-charged streams of electrons generated by the acceleration and conversion of electricity. E-beam sterilization may be used, for example, when the medicament is included in a gel form.

Other methods may also be used to sterilize the medicament and/or one or more components of the device, including, but not limited to, gas sterilization, such as, for example, with ethylene oxide or steam sterilization.

One or more of the components of the device can be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A device for dispensing a medicament, the device comprising:
   a housing having a proximal end, the housing having a container disposed within the housing, the container configured to hold a medicament, the container having a needle at a proximal end, and a stopper disposed within the container;
   a plunger having a distal end and a proximal end, the proximal end of the plunger configured to engage the stopper, the distal end of the plunger configured to engage a first resilient member and move the stopper within the container to dispense the medicament from the container and out of the needle;
   a carriage having at least a portion of the container disposed therein, the carriage rotatable relative to the housing;
   a collar having a distal end and a proximal end, the distal end of the collar configured to engage the carriage and cause rotation of the carriage, the proximal end of the collar configured to engage a second resilient member;
   a skin sensor having a distal end and a proximal end, the distal end of the skin sensor configured to engage the second resilient member, and the proximal end of the skin sensor configured to contact skin; and
   a cap configured to engage the proximal end of the housing and the skin sensor, the cap having a locking surface configured to lock with a locking surface of the skin sensor to reduce movement of the skin sensor, wherein when the cap is removed from the housing and an injection force is applied to the skin sensor, the second resilient member is compressed and engages the collar and causes the collar to rotate the carriage, on rotation of the carriage, the first resilient member engages the plunger to inject the medicament from the container and out of the needle.

2. The device of claim 1, wherein the locking surface of the cap comprises a recess or projection, and the skin sensor further comprises a skin sensor insert, the skin sensor insert comprising a recess or projection that locks with the recess or projection of the locking surface of the cap.

3. The device of claim 2, wherein the skin sensor insert comprises lugs configured to engage a U-slot in the carriage and/or slots in the skin sensor.

4. The device of claim 3, wherein the carriage has a proximal end and a distal end, the proximal end of the carriage configured to engage with the lugs of the skin sensor insert and the distal end of the carriage configured to engage with the collar.

5. The device of claim 4, wherein at the distal end of the carriage, the carriage further comprises a helical cam, the helical cam having a straight edge and an arcuate edge, the edges defining a point configured to receive the collar so that the collar can rotate the carriage.

6. The device of claim 5, wherein the second resilient member is a spring, which upon compression exerts a torque on the carriage causing the carriage to rotate.

7. The device of claim 3, wherein the carriage comprises a tubular body having a proximal end and a distal end, a lower portion at the proximal end of the tubular body, an upper portion at the distal end of the tubular body and a base between the upper portion and the lower portion of the tubular body.

8. The device of claim 7, wherein the proximal end of the carriage further comprises an abort rail, an injection rail and a lock rail, the rails spaced apart and next to one another.

9. The device of claim 8, wherein the lock rail is disposed between the abort rail and the injection rail.

10. The device of claim 9, wherein the lock rail comprises a U-shaped slot configured to engage the lugs of the skin sensor insert to reduce or prevent the skin sensor from moving when the device is dropped or shocked.

11. The device of claim 10, wherein when the cap is removed from the housing, and the injection force is applied to the skin sensor, the second resilient member is compressed and drives the skin sensor insert down a slope of the U-shaped slot and out of engagement with the lock rail.

12. The device of claim 7, wherein the lower portion of the tubular body of the carriage further comprises an abort rail, an injection rail and a lock rail, the rails disposed at the proximal end of the lower portion of the tubular body of the carriage, spaced apart and next to one another.

13. The device of claim 7, wherein the skin sensor insert further comprises an external pin and the skin sensor comprises an external slot and a cam face configured to allow the external pin of the skin sensor insert to run along the cam face of the skin sensor and engage with the external slot of the skin sensor.

14. The device of claim 3, wherein the distal end of the skin sensor further comprises a cam for engagement with the collar.

15. The device of claim 14, wherein the distal end of the collar further comprises a threshold face, the cam of the skin sensor causes the threshold face of the collar to rotate and engage with the carriage to generate a threshold force.

16. The device of claim 15, wherein the threshold force varies from about 9 N to about 23 N.

17. The device of claim 2, wherein the recess or projection of the cap comprises a triangular shaped cam.

18. The device of claim 17, wherein the recess or projection of the skin sensor insert is a W shaped cam configured to couple with the triangular shaped cam of the cap.

19. The device of claim 1, wherein the medicament comprises an analgesic agent, an anti-inflammatory agent, a hormone, a beta agonist agent, an alpha agonist agent, a beta antagonist agent, an alpha antagonist agent, a benzodiazepine, a glucose modulator, a narcotic, a narcotic antagonist, a cholinergic agent, an anti-cholinergic agent, a muscarinic agonist agent, a muscarinic antagonist agent, a steroid, a chloride salt, an iodide salt, a cholinesterase reactivator agent, a cholinesterase agonist, an antimicrobial agent, an anti-arrhythmic agent, a vasodilator agent, a vasoconstrictor agent, an anti-coagulant agent, a cardiovascular agent, an anti-parkinsonian agent, an anti-psychotic agent, an immunosuppressant agent, an antihistamine, or a combination thereof.

20. The device of claim 1, wherein the medicament comprises naloxone or glucagon.

21. The device of claim 1, wherein the medicament is an agent that is a beta agonist and an alpha agonist.

* * * * *